United States Patent [19]
Claremon et al.

[11] Patent Number: 5,451,578
[45] Date of Patent: Sep. 19, 1995

[54] FIBRINOGEN RECEPTOR ANTAGONISTS

[75] Inventors: David A. Claremon, Maple Glen; Nigel Liverton, Harleysville; John J. Baldwin, Gwynedd Valley, all of Pa.

[73] Assignee: Merck & Co., Inc., Rahway, N.J.

[21] Appl. No.: 289,974

[22] Filed: Aug. 12, 1994

[51] Int. Cl.⁶ .................. A61K 31/55; C07D 221/20
[52] U.S. Cl. ........................... 514/212; 514/278; 514/19; 546/16; 530/323; 540/543; 540/597
[58] Field of Search ............... 546/16; 514/212, 278, 514/19; 530/323; 540/543, 597

[56] References Cited

U.S. PATENT DOCUMENTS

| | | | |
|---|---|---|---|
| 5,227,490 | 7/1993 | Hartman et al. | 514/317 |
| 5,264,420 | 11/1993 | Duggan et al. | 514/19 |
| 5,272,158 | 12/1993 | Hartman | 514/323 |
| 5,281,585 | 1/1994 | Duggan et al. | 514/79 |
| 5,292,756 | 3/1994 | Duggan et al. | 514/331 |
| 5,294,616 | 3/1994 | Duggan et al. | 514/255 |
| 5,321,034 | 6/1994 | Duggan et al. | 514/323 |

FOREIGN PATENT DOCUMENTS

| | | | |
|---|---|---|---|
| 0479481A2 | 4/1992 | European Pat. Off. | C07K 5/10 |
| 2271567 | 4/1994 | United Kingdom | C07D 211/20 |
| WO94/08577 | 4/1994 | WIPO | A61K 31/38 |
| WO94/08962 | 4/1994 | WIPO | C07D 205/00 |

*Primary Examiner*—C. Warren Ivy
*Assistant Examiner*—Amelia Owens
*Attorney, Agent, or Firm*—Richard S. Parr; Melvin Winokur

[57] ABSTRACT

Compounds of the invention have the formula:

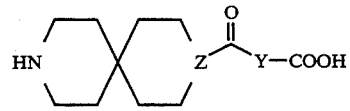

which have fibrinogen receptor antagonist activity, including, for example,

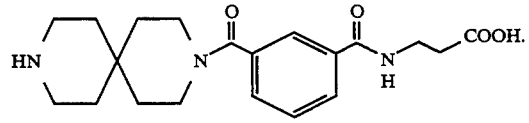

19 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothelial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and 4,578,079.

Rugged et al., *Proc. Nat'l Acad. Sci, U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gpIIb/IIIa complex. For example, Huang et al., *J. Biol Chem.*, 262, 16157–16163 (1987); Huang et al., *Biochemistry* 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gpIIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$—A—(W-$)_a$—X—$(CH_2)b$—$(Y)_c$—B—Z—COOR wherein $R^1$ is a guanidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention comprises compounds having the formula

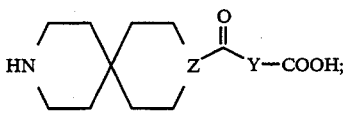

wherein
Z is a nitrogen atom or a carbon atom; and
Y is
  $C_{2-4}$ alkylenecarbonylamino $C_{1-3}$ alkylene, substituted or unsubstituted with
    phenyl $C_{1-2}$ alkyl,
    indolyl $C_{1-2}$ alkyl,
    $C_{1-6}$ alkylsulfonamino, or
    arylsulfonamino;
  $C_{2-4}$ alkylenecarbonylcyclo (amino $C_{2-4}$ alkylene);
  $C_{4-7}$ alkylene;
  $C_{0-4}$ alkylenephenyl $C_{0-4}$ alkylene;
  phenylsulfonylamino $C_{1-3}$ alkylene, substituted or unsubstituted with
    $C_{1-3}$ alkyl,
    $C_{1-4}$ alkylsulfonylamino, or
    $C_{1-2}$ alkylphenylsulfonylamino;
  phenylthio $C_{1-3}$ alkylene;
  phenylcarboxy $C_{1-3}$ alkylene;
  phenyl $C_{2-4}$ alkylene, substituted or unsubstituted with
    $C_{2-4}$ alkylsulfonylamino;
  phenylcarbonylamino $C_{1-3}$ alkylene, substituted or unsubstituted with
    phenyl $C_{1-2}$ alkyl,
    $C_{1-4}$ alkylsulfonylamino,
    $C_{13}$ alkyl, or
    a dipeptide;
  phenylcarbonylcyclo (amino $C_{2-4}$ alkylene);
  phenylhydroxy $C_{2-4}$ alkylene;
  amino $C_{1-7}$ alkylene, substituted or unsubstituted with
    phenyl $C_{1-2}$ alkyl;
  amino $C_{1-2}$ alkylenecarboxyamino $C_{2-3}$ alkylene substituted or
  unsubstituted with
    phenyl $C_{1-2}$ alkylene; or
    aminophenylcarbonylamino $C_{1-7}$ alkylene
and pharmaceutical salts thereof, and esters thereof.

The above definitions for Y represent moieties having two points of attachment. The first named pan of the moiety attaches to

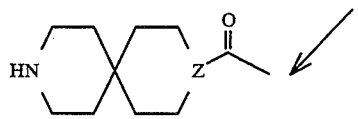

while the last named part of the moiety attaches to

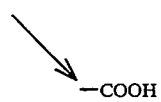

DETAILED DESCRIPTION OF THE INVENTION

One class of compounds of the invention has the formula

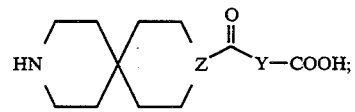

wherein
Z is a nitrogen atom or a carbon atom; and
Y is
  i)

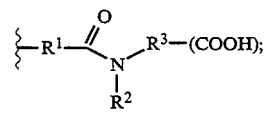

wherein
$R^1$ is $C_{2-4}$alkylene;
$R^2$ is hydrogen or phenyl $C_{1-2}$alkylene, or in combination with $R^3$, forms a heterocyclic ring substituted with COOH;
$R^3$ is $C_{1-3}$alkylene,

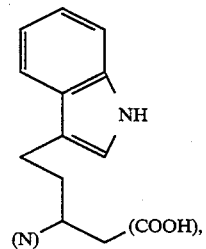

[structure showing phenethyl-substituted amino acid with (N) and (COOH)],

[structure: (HO)(O=)C-CH(-(N))-NH-S(=O)₂-(CH₂)₁₋₅CH₃], or

[structure: (HO)(O=)C-CH(-(N))-NH-S(=O)₂-C₆H₄-W]

wherein W is H, Me or Cl,
or in combination with R², forms a heterocyclic ring substituted with COOH, wherein the heterocyclic ring formed by R² and R³ is

[pyrrolidine-type ring with N, (n)]

where n is 1–3;
ii) C₄₋₇alkylene;
iii) C₀₋₄alkylenephenylC₀₋₄alkylene;
iv)

[phenyl-SO₂-R⁶];

wherein R⁶ is

[-NH-CH₂CH₂-(COOH)], [-NH-CH₂-(COOH)],

[-N(CH₃)-CH₂-(COOH)], [-(CH₂)₃-(COOH)]

[-NH-CH₂-CH(COOH)-NH-SO₂-(CH₂)₃CH₃] or

[-NH-CH₂-CH(COOH)-NH-SO₂-C₆H₄-CH₃];

v)

vi) [phenyl-S-CH₂CH₂-(COOH)];

vii) [phenyl-C(=O)-CH₂CH₂CH₂-(COOH)];

viii) [phenyl-CH₂CH₂CH₂-CH(COOH)-NH-SO₂-(CH₂)₃CH₃];

[phenyl-C(=O)-N(R⁷)-R⁸-(COOH)];

wherein
R⁷ is hydrogen or phenyl C₁₋₂alkyl, or in combination with R⁸ forms a heterocyclic ring substituted with COOH;
R⁸ is C₁₋₃alkylene,

[(HOOC)-CH(-CH₂(N))-NH-SO₂-(CH₂)₃-CH₃, CH(CH₃)(N)-CH₂-(COOH)],

[structure: phenylalanine amide with (N)-CH(COOH)- linkage, COOH],

[structure: phenylalanine methyl ester amide with (N)-CH(COOH)- linkage, OCH₃], or in combination with $R^7$ forms a heterocyclic ring substituted with COOH, wherein the heterocyclic ring formed by $R^7$ and $R^8$ is

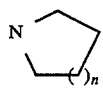

where n is 1-3;

ix)

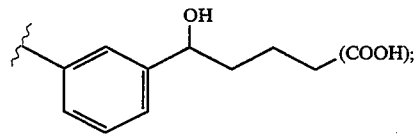

x)

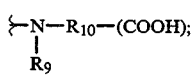

wherein
$R^9$ is hydrogen or phenyl $C_{1-2}$alkyl;
$R^{10}$ is

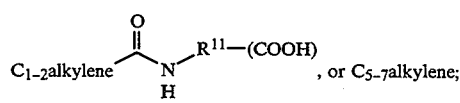

, or $C_{5-7}$alkylene;

$R^{11}$ is $C_{2-3}$alkylene optionally substituted with phenyl $C_{1-2}$alkyl; or xi)

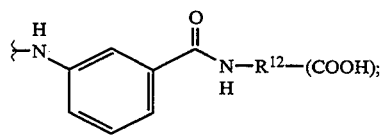

wherein
$R^{12}$ is $C_{1-3}$alkylene
and pharmaceutical salts thereof, and esters thereof.

The use of "(COOH)" and "(N)" for defining substituents such as Y, $R^3$ and $R^6$ is for the purpose of clearly representing the relationship of the defined substituent to the described compound. Unless otherwise indicated, the use of the symbol "—" indicates a bond.

In one subclass of compounds of the invention, the compounds have the formula

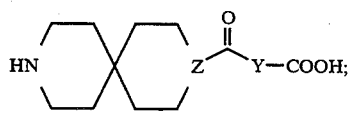

wherein
Z is a nitrogen atom or a carbon atom: and
Y is
i) $C_{0-4}$alkylphenyl$C_{0-4}$alkyl;
ii)

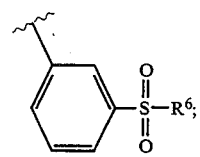

wherein
$R^6$ is

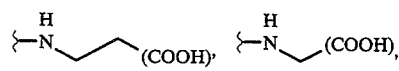

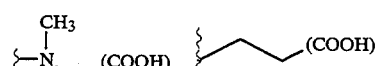

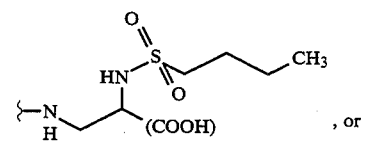

, or

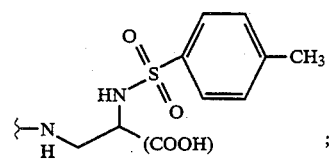

;

iii)

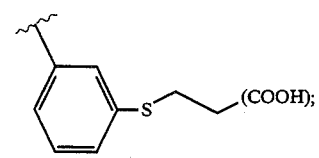

iv)

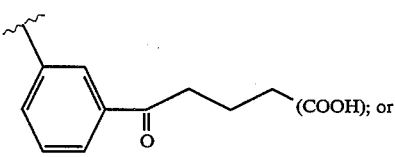

; or v)

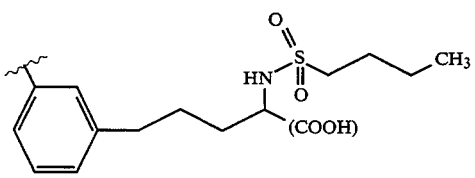

and pharmaceutical salts thereof, and esters thereof.

In another embodiment, the compounds have the formula

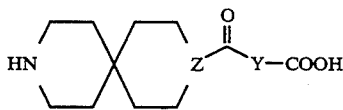

wherein

Z is a nitrogen atom; and

Y is $C_{0-4}$alkylenephenyl$C_{0-4}$alkylene;

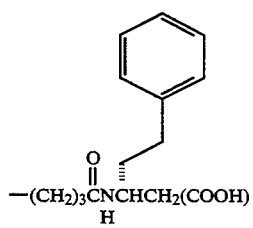

$-(CH_2)_3\overset{O}{\underset{H}{C}}N CHCH_2(COOH)$, or

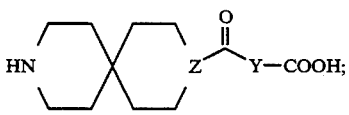

$-(CH_2)_3\overset{O}{\underset{H}{C}}N CHCH_2(COOH)$ and pharmaceutical salts thereof, and esters thereof.

In another embodiment of this subclass, the compounds have the formula

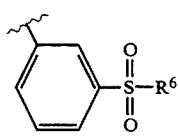

wherein

Z is a carbon atom; and

Y is i) $C_{1-4}$alkylenephenyl$C_{0-2}$alkylene;

ii)

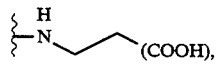

wherein $R^6$ is

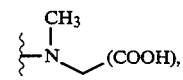

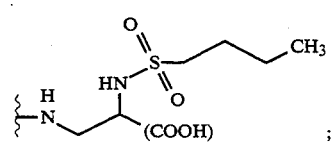

or

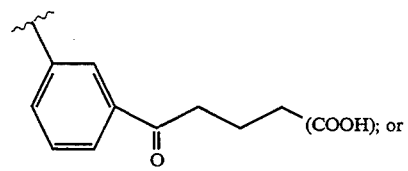

iii)

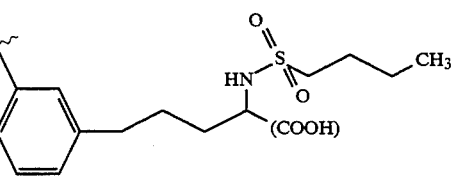

iv)

and pharmaceutical salts thereof, and esters thereof.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Exemplary compounds of the invention are those selected from the following group of compounds ($IC_{50}$ for some of these compounds are shown below the compound structure):

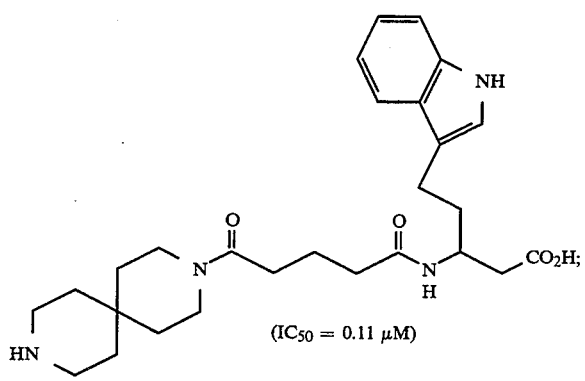
(IC$_{50}$ = 0.11 μM)
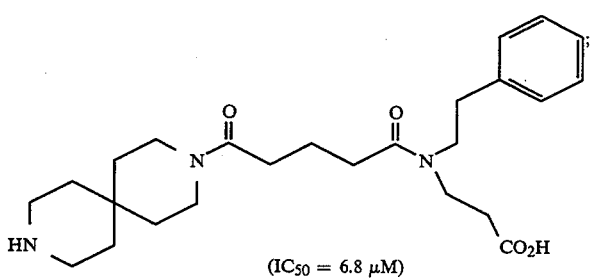
(IC$_{50}$ = 6.8 μM)
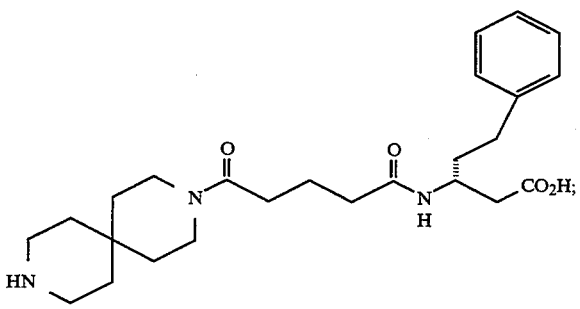
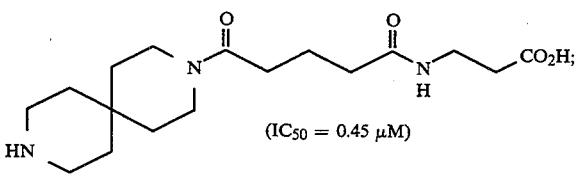
(IC$_{50}$ = 0.45 μM)
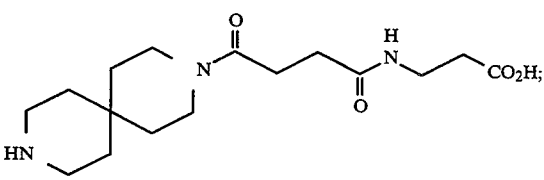
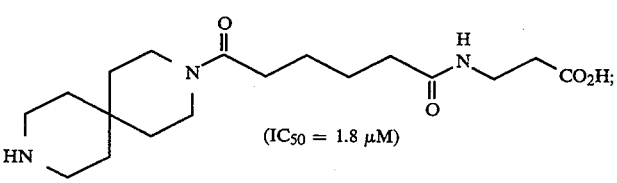
(IC$_{50}$ = 1.8 μM)

-continued
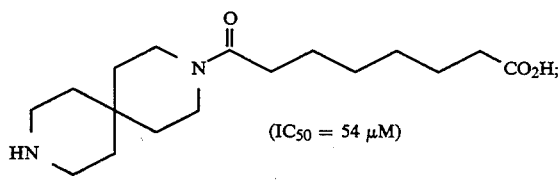
(IC$_{50}$ = 54 μM)
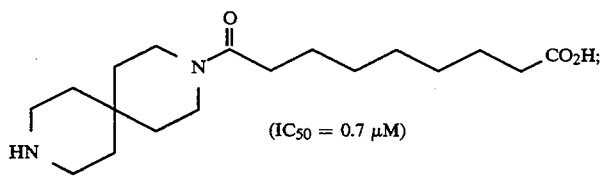
(IC$_{50}$ = 0.7 μM)
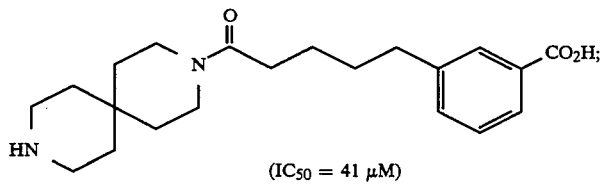
(IC$_{50}$ = 41 μM)
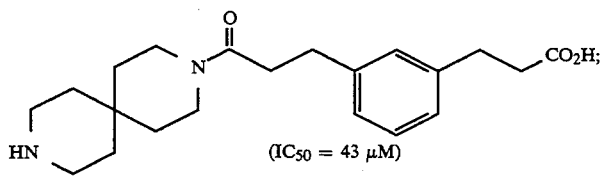
(IC$_{50}$ = 43 μM)
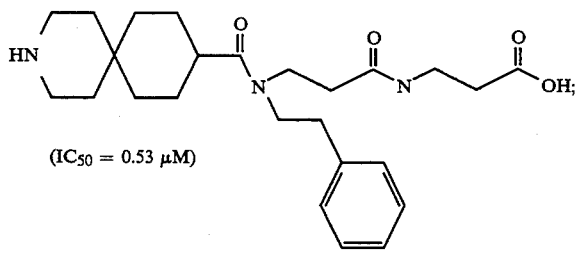
(IC$_{50}$ = 0.53 μM)
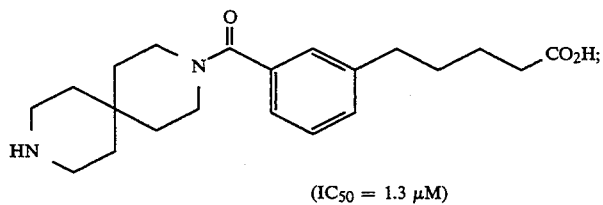
(IC$_{50}$ = 1.3 μM)
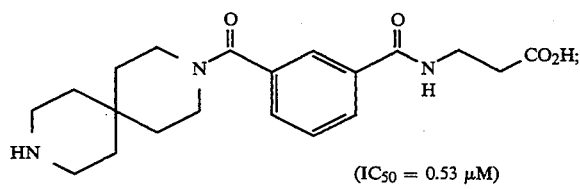
(IC$_{50}$ = 0.53 μM)
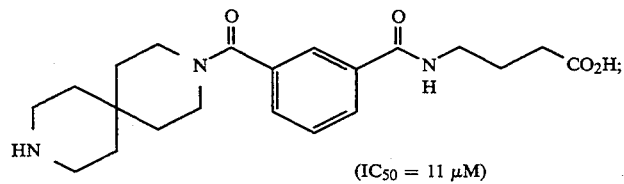
(IC$_{50}$ = 11 μM)

-continued
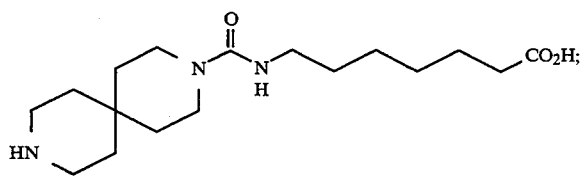
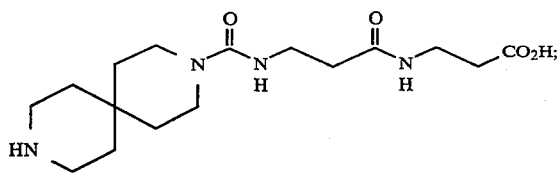
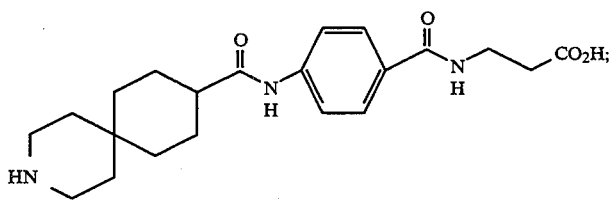
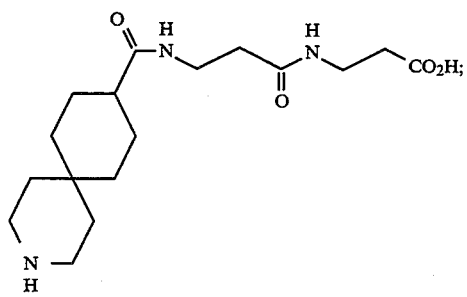
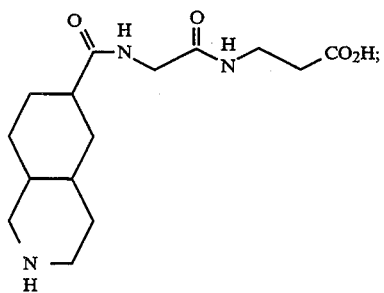
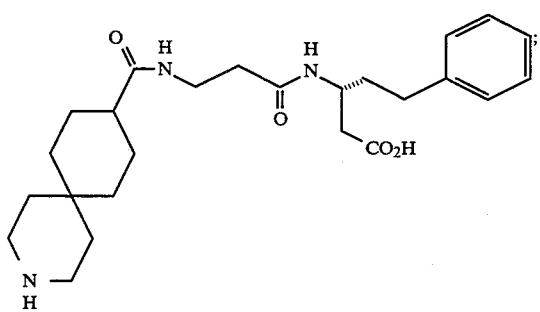

-continued
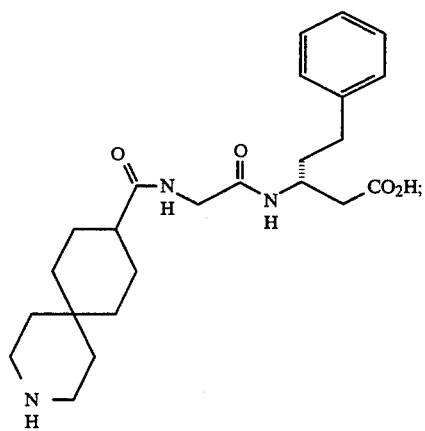
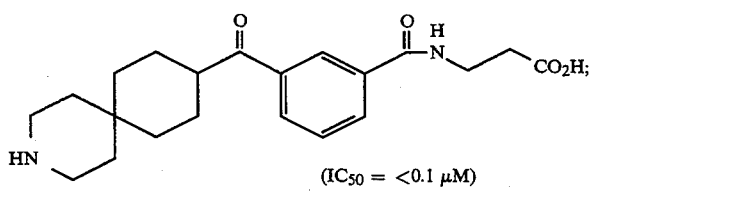
($IC_{50}$ = <0.1 μM)
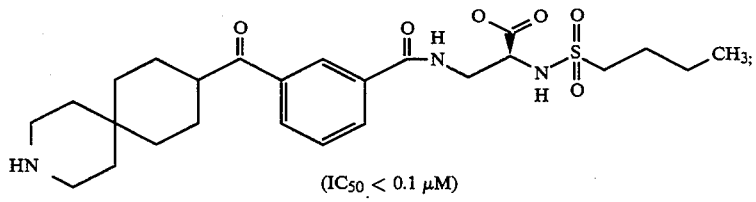
($IC_{50}$ < 0.1 μM)
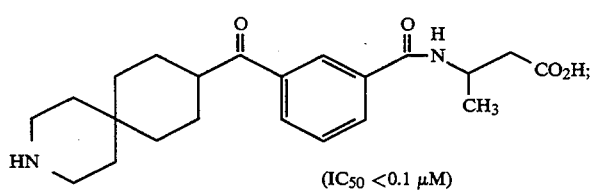
($IC_{50}$ <0.1 μM)
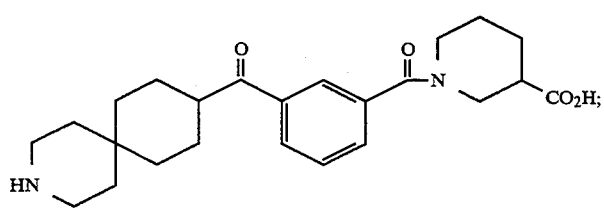
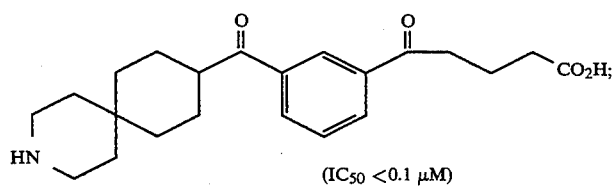
($IC_{50}$ <0.1 μM)
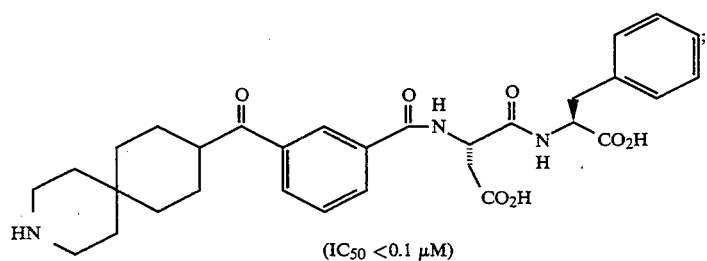
($IC_{50}$ <0.1 μM)

-continued
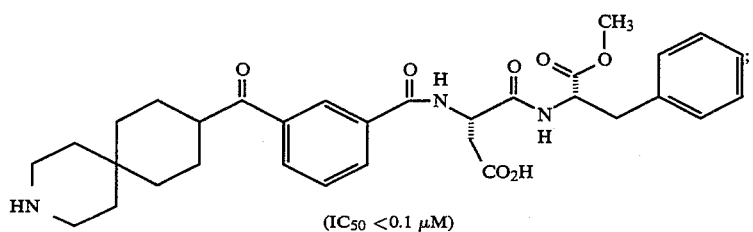
(IC$_{50}$ <0.1 μM)
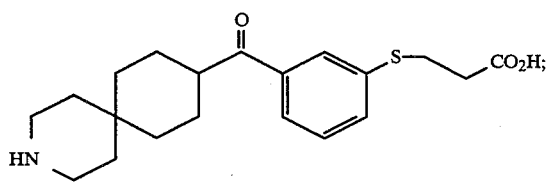
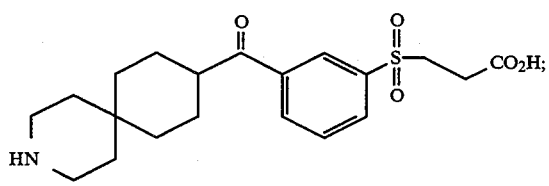
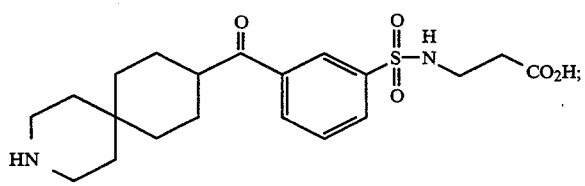
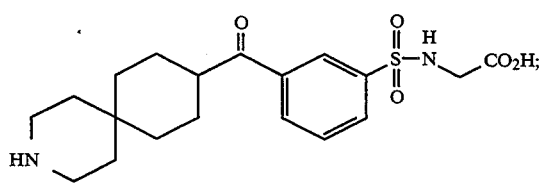
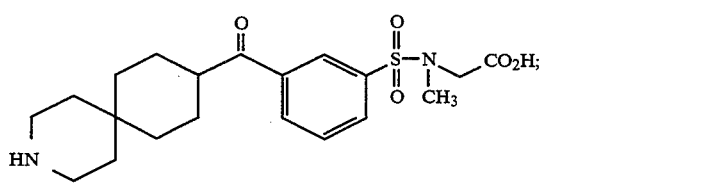
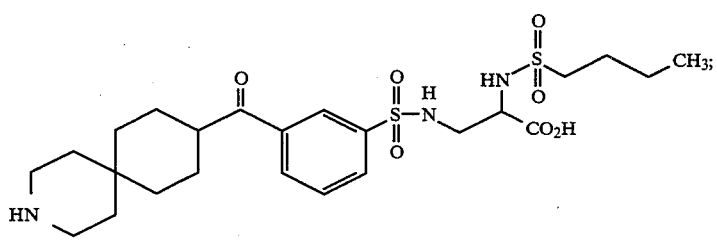
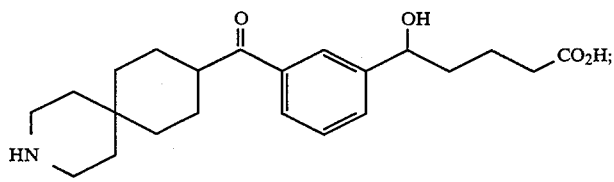

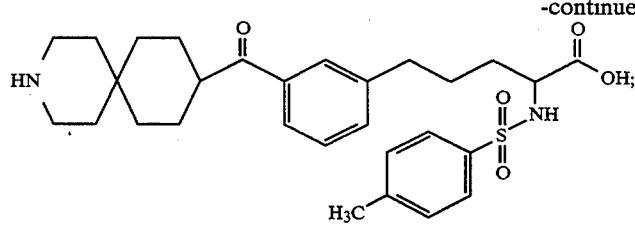

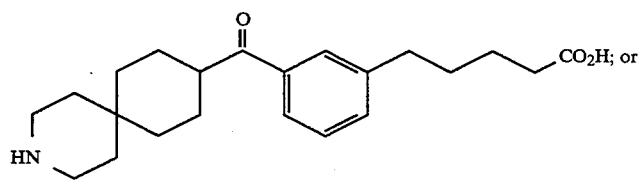

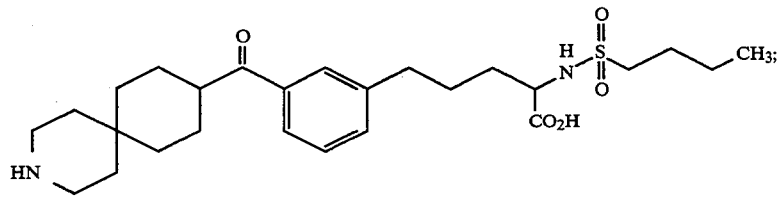

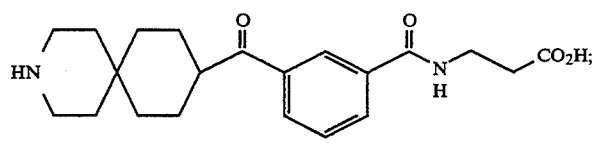

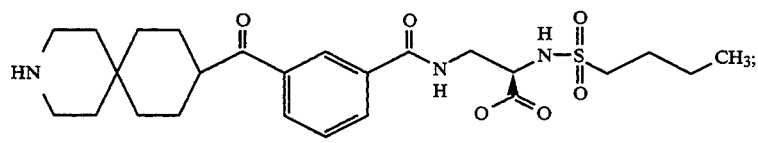

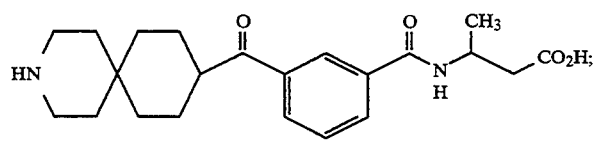

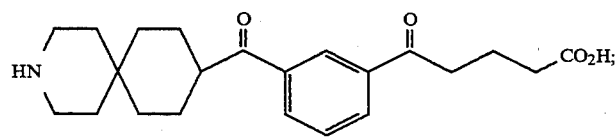

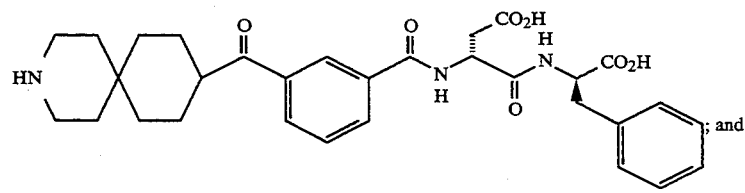

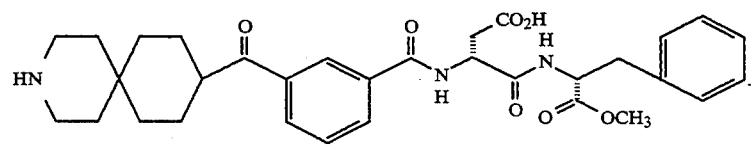

The term "pharmaceutically acceptable salts" shall mean non-toxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Prodrugs, such as ester deriviatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include streptokinase and tissue plasminogen activator. The term "platelet anti-aggregation agent" includes, for example, aspirin, ticlopidine, and dipyridamole.

In the schemes and examples below, various reagent symbols have the following meanings:

BOC(Boc): t-butyloxycarbonyl.
Pd-C: palladium on activated carbon catalyst.
DMF: dimethylformamide.
DMSO: dimethylsulfoxide.
CBZ: carbobenzyloxy.
$CH_2Cl_2$: methylene chloride.
$CHCl_3$: chloroform.
EtOH: ethanol.
MeOH: methanol.
tBu: tert butyl.
EtOAc: ethyl acetate.
HOAc: acetic acid.
BOP: benzotriazol-1-yloxytris(dimethylamino)phosphonium, hexafluorophosphate.
EDC: 1-(3-Dimethylaminopropyl)-3-ethylcarbodiimide.
Oxone: potassium peroxymonosulfate.
LDA: lithium diisopropylamide.
Me: methyl.
Et: ethyl.
Bu: butyl.

Therapeutic Treatment

Compounds of the invention may be used for inhibiting integrin protein-complex function relating to cell attachment activity. They may be administered to patients where inhibition of human or mammalian platelet aggregation or adhesion is desired.

Certain compounds of the invention are eliminated from circulation rapidly and are particularly useful in inhibiting platelet aggregation in situations where a strong antithrombotic of short duration or effectiveness is needed. Thus, these compounds may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, sublingual, intranasal or intramuscular form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary and other arteries and after coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 1.0–100 mg/kg/day and most preferably 1–20 mg/kg/day. Intravenously, the most preferred doses will range from about 1 to about 10 µg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintergrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulation agents, including antiplatelet agents such as heparin, aspirin, warfarin, dipyridamole and other compounds and agents known to inhibit blood clot formation, or thrombolytic agents such as plasminogen activators or streptokinase, to achieve synergistic effects in the treatment of various vascular pathologies.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

In addition to the following preparative procedures, several examples of in vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

EXAMPLE 1

3-[5-(3,9-Diazaspiro[5.5]undec-3-yl)-5-oxopentanoylamino] propionic acid

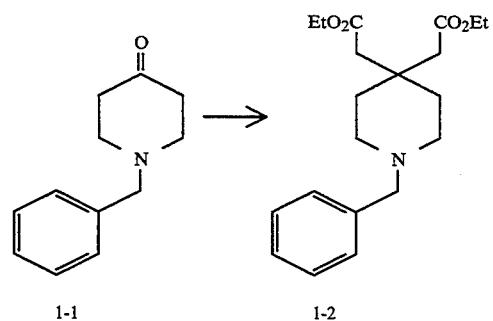

Ethanol (120 mL) was cooled in ice and ammonia bubbled through to give a saturated solution. 1-Benzyl-4-piperidone 1-1 (40.0 g, 211 mmol) and ethyl cyanoacetate (47.8 g, 423 mmol) were added, the reaction vessel stoppered and stored at 0° C. overnight. The solid was collected, washed with ethanol and ether and dried in vacuo to give a yellow solid (68.86 g). The solid (58.86 g) was dissolved in a mixture of sulfuric acid (70 mL, 98%) and water (60 mL) and heated under reflux for three days, the mixture cooled and most of the water evaporated. The residue was azeotroped with ethanol (4×750 mL), further ethanol (500 mL) added and the mixture heated under reflux for 20 h, cooled in ice and sodium carbonate (100 g) added slowly with vigorous stirring. The ethanol was evaporated under reduced pressure, water (800 mL) added and the mixture extracted with methylene chloride (3×400 mL). The combined organic extracts were dried (Na$_2$SO$_4$) and the solvent evaporated to give the diester 1-2 (37.51 g). A small portion of this was purified by flash column chromatography.

NMR (300 MHz, CDCl₃) δ: 7.2–7.4 (m, 5H), 4.11 (q, J=7.3 Hz, 4H), 3.50 (s, 2H), 2.56 (s, 4H), 2.4 (m, 4H), 1.7 (m, 4H), 1.24 (t, J=7.3 Hz, 6H).

Step B:

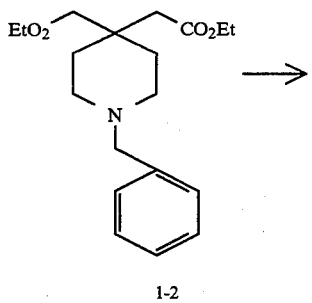

1-2

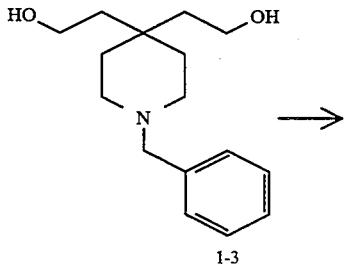

1-3

A solution of the diester 1-2 (12.2 g, 35 mmol) in ether (25 mL) was added to a cooled (−30° C.) and stirred suspension of LiAlH₄ (2.1 g, 55 mmol) in ether (400 mL), under argon. THF (60 mL) was added and the reaction mixture allowed to warm to room temperature. After recooling to 0° C., water (2.2 mL,), 1M NaOH (4.4 mL) and water (5 mL) were added, the reaction mixture stirred vigorously for 30 min. and the solid filtered off, washing well with ether. The combined filtrates were evaporated to afford a white solid which was tritutrated with ether to give 8 g of product 1-3.

m.p. 75°–78° C. NMR (300 MHz, CDCl₃) δ: 7.2–7.4 (m, 5H), 3.7 (t, J=6.8 Hz, 4H), 3.52 (s, 2H), 2.7 (brs, 2H), 2.43 (m, 4H), 1.66 (t, J=6.8 Hz, 4H), 1.5 (m 4H).

Step C:

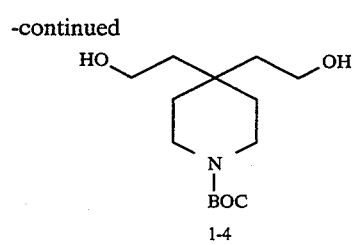

1-3

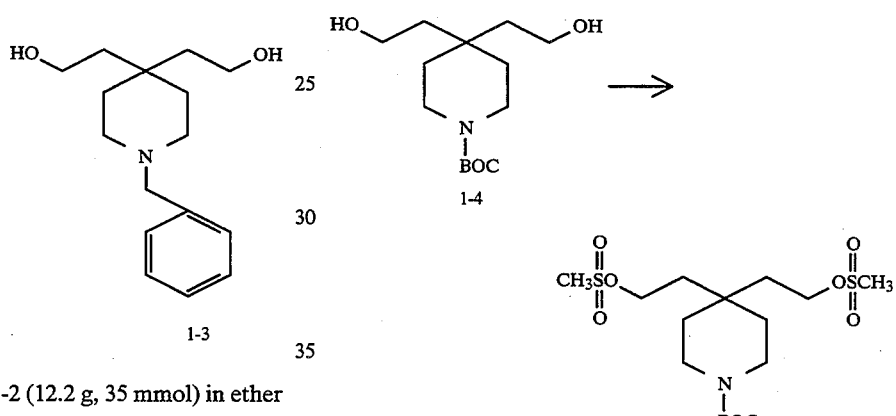

The benzylamine 1-3 (2.07 g, 7.9 mmol) was dissolved in methanol (60 mL), BOC₂O (1.72 g, 7.9 mmol) added and the mixture hydrogenated at 50 psi over 10% palladium hydroxide on charcoal (200 mg) for 18 hours. The reaction mixture was filtered through celite, washed with methanol and the filtrate evaporated to give the product 1-4 (2.0 g).

NMR (300 MHz, CDCl₃) δ: 3.7 (m, 4H), δ3.3.3 (m, 6H), 1.65 (t, J=6.8 Hz, 4H), 1.41 (s, 9H).

Step D:

The diol 1-4 (2.41 g, 8.9 mmol) was dissolved in dichloromethene (50 mL), the solution cooled to −20° C. under argon before addition of triethylamine (3.7 mL, 26 mmol) and methanesulfonyl chloride (1.6 mL, 20 mmol). After 30 min., the reaction mixture was poured into ice cold 10% citric acid and extracted with ether (×3). The combined extracts were washed with water, saturated NaHCO₃ and brine, dried (MgSO₄) and the solvent evaporated to afford the bis mesylate 1-5 (3.2 g).

NMR (300 MHz, CDCl₃) δ: 4.32 (t, J=7.1 Hz, 4H), 3.4 (m, 4H), 3.04 (s, 6H), 1.89 (t, J=7.1 Hz, 4H).

Step E:

The bis mesylate 1-5 (3.2 g, 7.5 mmol) was dissolved in methanol (10 mL) and ammonium hydroxide solution (6 mL) added. The mixture was heated to 50° C. in a sealed tube for 24 h, cooled to room temperature, poured into ice cold 1N sodium hydroxide solution and extracted with ethyl acetate (×3). The combined extracts were dried (K₂CO₃), the solvent evaporated and the crude product purified by flash column chromatography on silica (20:15:5: 1, ether:ethanol:water: ammonium hydroxide solution) to give 1.17 g product 1-6.

NMR (300 MHz, CDCl₃) δ: 3.4 (m, 4H):, 2.8 (m, 4H), 2.2 (brs, 2H), 1.4 (brs, 15H).

Step F:

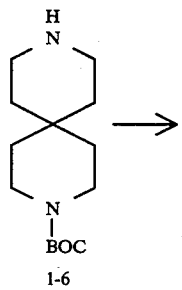

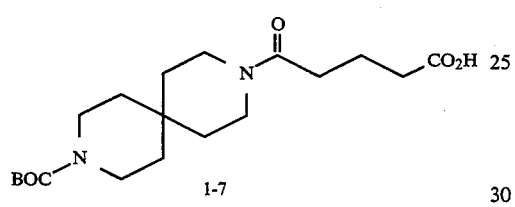

The amine 1-6 (140 mg, 0.55 mmol) was dissolved in dichloromethane (5 mL), cooled to 0° C. and triethylamine (140 mL, 1 mmol) added, followed by a solution of glutaric anhydride (68 mg, 0.6 mmol) in dichloromethane (3 mL). After stirring for 30 min., the mixture was poured into ice cold 10% citric acid solution and extracted with ethyl acetate (×3). The combined extracts were washed with water and brine, dried (MgSO4) and the solvent evaporated to give the product 1-7 (200 mg).

NMR (300 MHz, CDCl₃) δ: 3.6 (brs, 2H), 3.4 (m, 4H), 2.45 (m, 4H), 1.95 (quintet J=7.1 Hz, 2H), 1.4 (brs, 19H).

Step G:

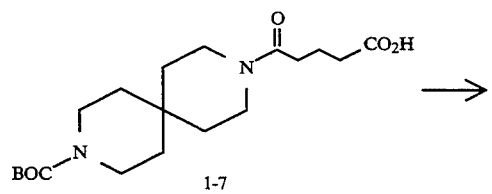

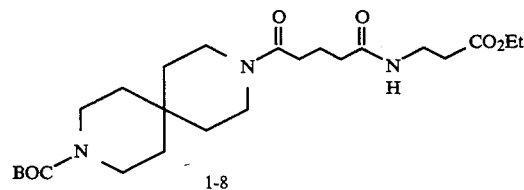

The acid 1-7 (185 mg, 0.52 mmol) was dissolved in DMF (1.4 mL) and β-alanine ethyl ester hydrochloride (160 mg, 1.04 mmol), HOBt (140 mg, 1.04 mmol), triethylamine (150 μL 1.1 mmol) and EDC (200 mg, 1.04 mmol) added. The reaction mixture was stirred at room temperature for 18 hours, poured into ice cold 10% citric acid solution and extracted with ethyl acetate. The organic phase was washed with water, saturated NaHCO₃ solution and brine and the aqueous phases back extracted with ethyl acetate. The combined extracts were dried (MgSO4) and the solvent evaporated to give, after ether tritration, the product 1-8. (170 mg).

NMR (300 MHz, CDCl₃) δ: 6.45 (brs, 1H), 4.15 (q, J=7.1 Hz, 2H), 3.3–3.6 (m, 10H), 2.53 (t, J=6.3 Hz, 2H), 2.40 (t, J=7.3 Hz, 2H), 2.26 (t, J=7.1 Hz, 2H), 1.93 (q, J=7.1 Hz, 2H), 1.4 (brs, 16H), 1.25 (t, 3H).

Step H:

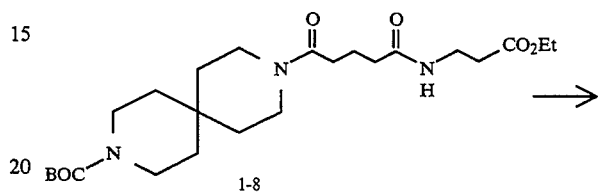

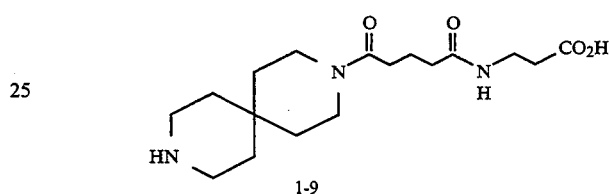

The ester 1-8 (170 mg, 0.31 mmol) was dissolved in THF (3 mL) and 1M LiOH (2 mL) added. The mixture was stirred vigorously at room temperature for 2 hours, poured into ice cold 10% citric acid solution and extracted with ethyl acetate. The organic layer was washed with water and brine and the aqueous phases back extracted with ethyl acetate. The combined extracts were dried (MgSO4) and solvent evaporated to give, after ethyl acetate trituration, 130 mg of solid. 80 mg of this was dissolved in ethyl acetate (10 mL) and the solution cooled to 0° C. before bubbling HCl through for 30 min. The volatiles were evaporated to give the product 1-9.

NMR (300 MHz, CD₃OD) δ: 8.05 (brs<1H), 3.47–3.58 (m, 4H), 3.35–3.45 (m, 2H), 3.2 (m, 4H), 2.48 (t, J=6.8 Hz), 2.38 (t, J=8.1 Hz, 2H), 2.21 (t, J=7.1 Hz, 2H), 1.45–1.9 (m, 10H).

EXAMPLE 2

3-[4-(3,9-Diazaspiro[5.5]undec-3-yl)-4-oxobutanoylamino] propionic acid

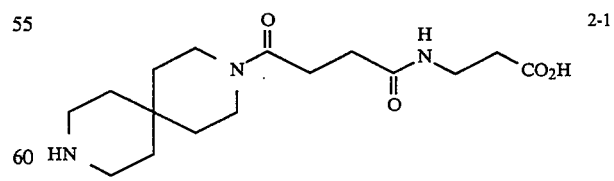

was prepared substantially as described in Example 1, but replacing glutaric anhydride with succinic anhydride in Step F.

NMR (300 MHz, D₂O) δ: 3.4 (m, 4H), 3.27 (t, J=6.6 Hz, 2H), 3.05 (m, 4H), 2.54 (t, J=6.8 Hz, 2H), 2.42 (t, J=6.3 Hz, 2H), 2.32 (t, J=6.6 Hz, 2H), 1.3–1.7 (m, 8H).

EXAMPLE 3

3-[5-(3,9-Diazaspiro[5.5]undec-3-yl)-5-oxopentanoylamino]-5-(1H-indol-3-yl)pentanoic acid
Step A:

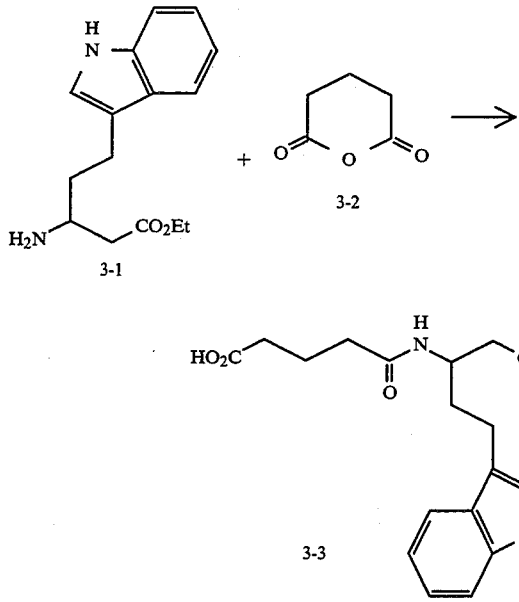

Glutaric anhydride 3-2 (210 mg, 1.84 mmol) was added to a stirred solution of ethyl 5-(3-indolyl)-3-aminopentanoate (European Publication 478362) 3-1 (479 mg, 1.84 mmol) in THF (10 mL). After 30 min., the volatiles were evaporated and the residue partitioned between ethyl acetate and ice cold 10% citric acid solution. The organic phase was washed with water and brine, dried (MgSO$_4$) and the solvent evaporated to give product 3-3. Yield 738 mg.

NMR (300 MHz, CDCl$_3$) δ: 8.17 (brs, 1H), 7.55 (d, 7.6 Hz, 1H), 7.34 (d, J=8.1 Hz, 1H), 7.17 (dt, J=1.0, 8.3 Hz, 1H), 7.11 (dt, J=1.2, 8.1 Hz, 1H), 7.04 (brd 1H), 6.33 (d, J=9.0 Hz, 1H), 4.38 (m, 1H), 4.1 (q, 2H), 2.7–2.9 (m, 2H), 2.45–2.62 (m, 2H), 2.43 (t, J=7.1 Hz, 2H), 2.23 (t, J=7.3 Hz, 2H), 1.8–2 (m, 4H), 1.25 (t, 3H).
Step B:

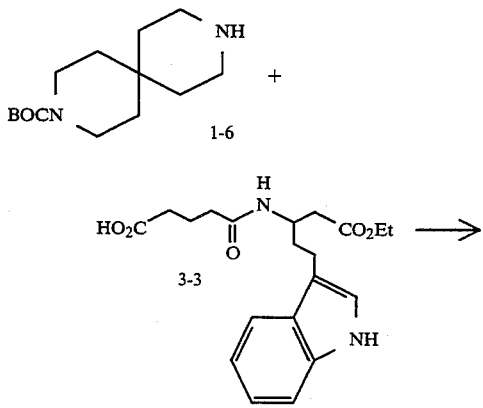

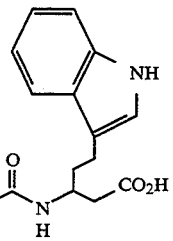

The acid 3-3 and amine 1-6 were coupled and deprotected as described in Example 1, Steps G-H.

NMR (400 MHz, D$_2$O) δ: 7.57 (d, J=8 Hz, 1H), 7.45 (d, J=8 Hz, 1H), 7.05–7.25 (m, 3H), 4.3 (m, 1H), 3.2–3.35 (m, 2H), 2.8–3.15 (m, 6H), 2.75 (t, J=8 Hz, 2H), 2.45 (m, 2H), 2.2–2.4 (m, 4H), 1.75–2.05 (m, 4H), 1.0–1.6 (m, 8H).

EXAMPLE 4

3-[5-(3,9-Diazaspiro[5.5]undec-3-yl)-5-oxopentanoylamino]-5-phenyl pentanoic acid

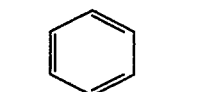

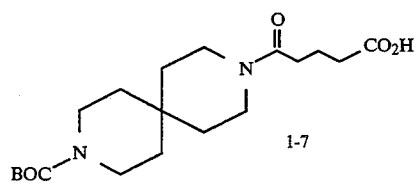

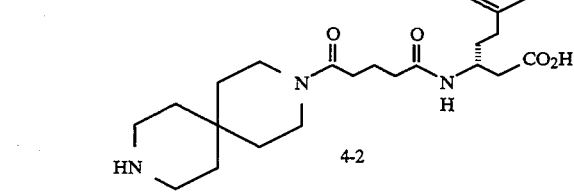

The acid 1-7 (Example 1, Step F) and amino ester (European Publication 478362) 4-1 were coupled and deprotected as described in Example 1, Steps G-H to afford the product 4-2.

NMR (300 MHz, D$_2$O) δ: 7.0–7.25 (m, 5H), 4.0 (m, 1H), 3.35 (m, 4H), 3.0 (m, 4H), 2.4–2.6 (m, 3H), 2.2–2.4 (m, 3H), 2.07 (t, J=7.3 Hz, 2H), 1.45–1.8 (m, 8H), 1.35 (m, 4H).

EXAMPLE 5

3-[6-(3,9-Diazaspiro[5.5]undec-3-yl)-6-oxohexanoylamino] propionic acid
Step A:

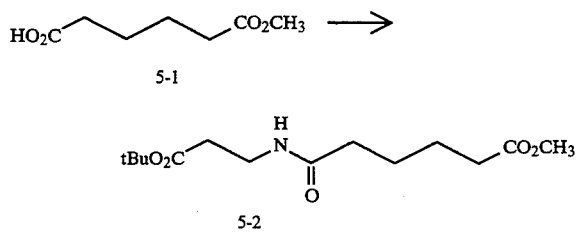

5-1

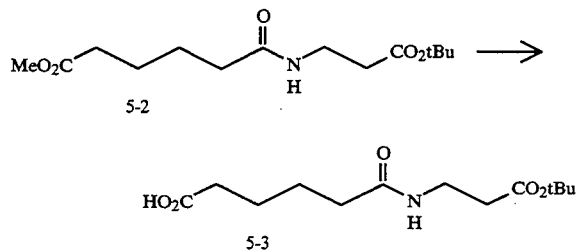

5-2

Adipic acid monomethyl ester 5-1 (2.66 mL, 18 mmol) was dissolved in DMF (30 mL) and triethylamine (2.1 mL, 15 mmol), HOBt (2.43 g, 18 mmol), β-alanine t-butyl ester hydrochloride (1.64 g, 9.02 mmol) and EDC (3.43 g, 18 mmol) added. The reaction mixture was stirred at room temperature for 18 hours, poured into ice cold 10% citric acid and extracted with ethyl acetate. The organic phase was washed with water, saturated NaHCO₃ solution and brine, the aqueous phases back extracted with ethyl acetate and the combined extracts dried (MgSO₄) and solvent evaporated. Product 5-2 was purified by flash column chromatography on silica. Yield 2.18 g.

NMR (300 MHz, CDCl₃) δ: 6.16 (brs, 1H), 3.67 (s, 3H), 3.47 (q, J=5.9 Hz, 2H), 2.44 (t, J=6.3 Hz, 2H), 2.33 (m, 2H), 2.18 (m, 2H), 1.6–1.7 (m, 4H), 1.45 (s, 9H).

Step B:

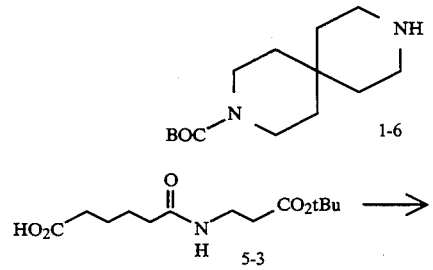

The methyl ester 5-2 (1.0 g, 3.5 mmol) was dissolved in THF (5 mL) and 1.0M lithium hydroxide solution (3.5 mL) added. The reaction mixture was stirred at room temperature for 3 hours, poured into ice cold 10% citric acid solution and extracted with ethyl acetate. The organic phase was washed with water and brine, the aqueous phases back extracted with ethyl acetate and the combined extracts dried (MgSO₄) and solvent evaporated to a solid 5-3.

NMR (300 MHz, CDCl₃) δ: 6.2 (brs, 1H), 3.45 (q, 2H), 2.45 (t, J=6.1 Hz, 2H), 2.37 (m, 2H), 2.20 (m, 2H), 1.65 (m, 4H), 1.43 (s, 9H).

Step C:

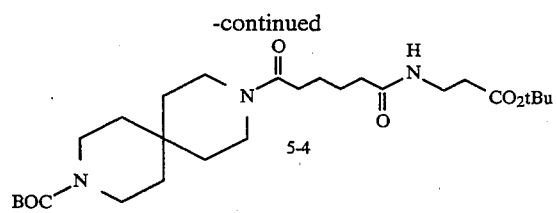

The acid 5-3 and amine 1-6 were coupled as described in Example 1, Step G.

NMR (300 MHz, CDCl₃) δ: 6.4 (brs, 1H), 3.3–3.6 (m, 10H), 2.45 (t, J=6 Hz, 2H), 2.35 (m, 2H), 2.20 (m, 2H), 1.6 (m, 4H), 1.45 (brs, 24H).

Step D:

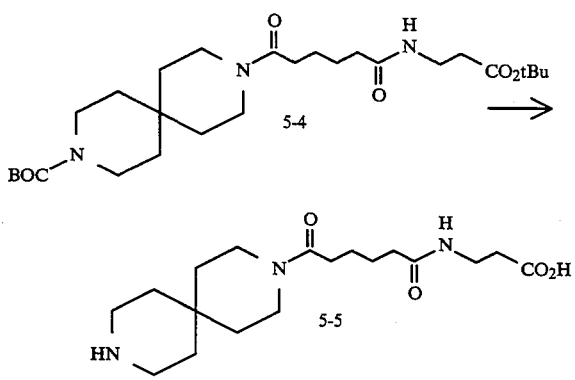

The ester 5-4 (610 mg, 1.17 mmol) was dissolved in dichloromethane, the solution cooled to −10° C. and trifluoroacetic acid (5 mL) added. The reaction mixture was allowed to warm to room temperature and stirred for 2 hours. The volatiles were evaporated and the residue 5-5 purified by flash column chromatography.

CHN: Calc. for 1.0 H₂O C, 58:19; H, 8.85; N, 11.22 Found: C, 58.19; H, 8.95; N, 11.31

NMR (300 MHz, CD₃Cl) δ: 3.4 (brs, 4H), 3.21 (t, J=7.1 Hz, 2H), 3.06 (brt, 4H), 2.29 (brt, J=7.3 Hz, 2H), 2.22 (t, J=7.1 Hz, 2H), 2.10 (brt, J=6.8 Hz, 2H), 1.6 (m, 4H), 1.4 (m, 8H).

EXAMPLE 6

3-[3-(3,9-Diazaspiro[5.5]undecane-3-carbonyl)-benzoylamino] propionic acid

Step A:

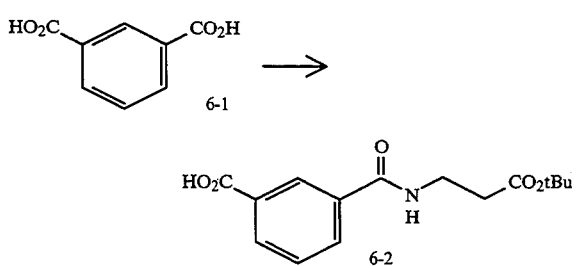

Isophthalic acid 6-1 (3.32 g, 22 mmol) was dissolved in DMF (30 mL) and β-alanine t-butyl ester hydrochloride (2.0 g, 11 mmol), HOBt (2.97 g, 22 mmol), diisopropylethylamine (2.61 mL, 15 mmol) and EDC (4.2 g, 22 mmol) added. The reaction mixture was stirred at room temperature for 18 hours, poured into 10% citric acid solution and extracted with ethyl acetate. The organic layer was washed with water and brine, the aqueous phases back extracted with ethyl acetate and the combined extracts dried (MgSO₄) and evaporated. The residue was partitioned between sodium bicarbonate solution and ethyl acetate, the aqueous solution was then adjusted to pH 6 with citric acid and extracted. Addition of more citric acid solution and extraction afforded, after drying and evaporation 700 mg of pure acid 6-2.

NMR (300 MHz, CD₃OD) δ: 8.7 (brs, 1H), 8.47 (brs, 1H), 8.18 (dt, J=1.2, 7.6 Hz, 1H), 8.02 (dt, J=1.2, J=7.8 Hz, 1H), 7.58 (t, J=7.8 Hz, 1H), 3.6 (m, 2H), 2.58 (t, J=6.8 Hz, 2H), 1.45 (s, 9H).

Step B:

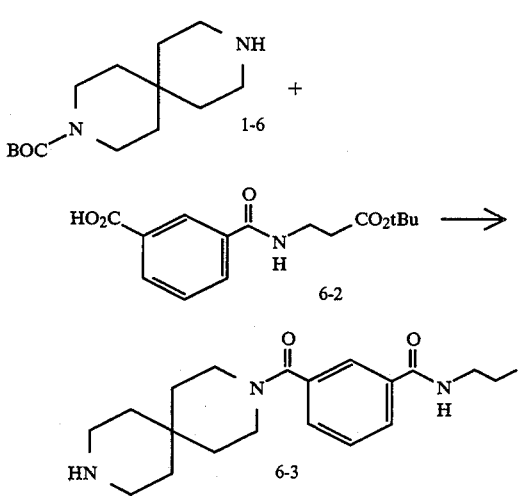

The acid 6-2 and amine 1-6 were coupled as described in Example 1, Step G and deprotected as described in Example 5, Step D.

NMR (300 MHz, D₂O) δ: 7.65 (m, 1H), 7.53 (s, 1H), 7.4 (m, 2H), 3.5 (m, 2H), 3.41 (t, J=6.8 Hz, 2H), 3.2 (m, 2H), 3.0 (m, 4H), 2.33 (t, J=6.8 Hz, 2H), 1.2–1.7 (m, 8H).

EXAMPLE 7

5-[3-(3,9-Diazaspiro[5.5]undecane-3-carbonyl)phenyl]-pentanoic acid

Step A:

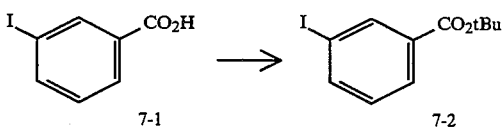

3-Iodobenzoic acid 7-1 (2.48 g, 10 mmol) was dissolved in DMF (10 mL) and carbonyldiimidazole (1.15 g, 10 mmol) added. The reaction mixture was heated to 40° C. for 1 hour followed by addition of t-butanol (1.48 g, 20 mmol) and DBU (1.52 g, 10 mmol) and heating at 40° C. for a further 18 hours. The reaction mixture was poured into ice cold 10% citric acid solution and extracted with ether. The organic phase was washed with citric acid solution, water and saturated NaHCO₃ solution. The aqueous phases were back extracted with ether and the combined extracts dried (MgSO₄), the solvent evaporated and the residue 7-2 purified by flash column chromatography. Yield 2.4 g.

NMR (300 MHz, CDCl₃) δ: 8.3 (s, 1H), 7.95 (dd, 1H), 7.85 (dd, 1H), 7.15 (t, J=7.8 Hz, 1H), 1.59 (s, 9H).

Step B:

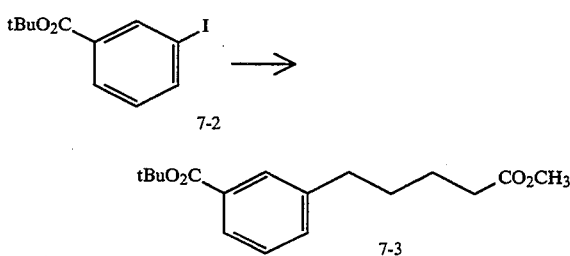

t-Butyl 3-iodobenzoate 7-2 (1.45 g, 4.78 mmol) and methyl 4-pentynoate (540 mg, 4.78 mmol) were dissolved in diethylamine (10 mL) and CuI (88 mg, 0.46 mmol) added, followed by bis(triphenylphosphine)-palladium (II) chloride (160 mg, 0.23 mmol). The reaction mixture was stirred for 2 hours, the volatiles evaporated and the residue purified by flash chromatography. The resulting oil (1.3 g) was dissolved in ethyl acetate (50 mL) and the solution hydrogenated at 50 psi over 10% palladium/charcoal until reaction was complete as judged by HPLC. The catalyst was removed by filtration through celite and the filtrate evaporated to give the product 7-3. Yield 1.2 g.

NMR (300 MHz, CDCl₃) δ: 7.8 (m, 2H), 7.35 (m, 2H), 3.66 (s, 3H), 2.65 (m, 2H), 2.35 (m, 2H), 1.65 (m, 4H), 1.60 (s, 9H).

Step C:

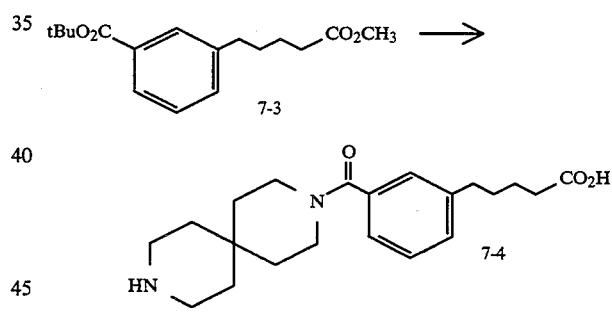

The t-butyl ester 7-3 was removed under the conditions described in Example 5, Step D and the resulting acid coupled and deprotected as described in Example 1, Step G and H.

CHN: Calc. for 1.35 H₂O: C, 65.88; H, 8.61; N, 7.32
Found: C, 65.87; H, 8.41; N, 7.08

NMR (300 MHz, D₂O) δ: 7.25 (m, 2H), 7.05 (m, 2H), 3.6 (m, 2H), 3.2 (m, 2H), 3.05 (m, 4H), 2.52 (t, J=8 Hz, 2H), 2.02 (t, J=8 Hz, 2H), 1.3–1.7 (m, 12H).

EXAMPLE 8

3-{[5-(3,9-Diazaspiro[5.5]undec-3-yl)-5-oxopentanoyl] phenethylamino} propionic acid

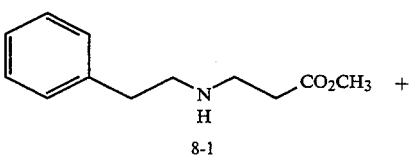

-continued

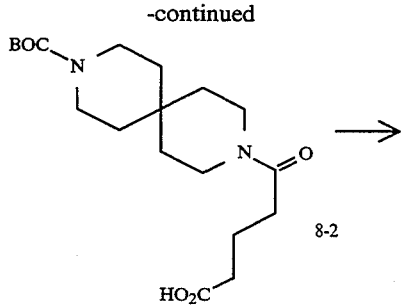

8-2

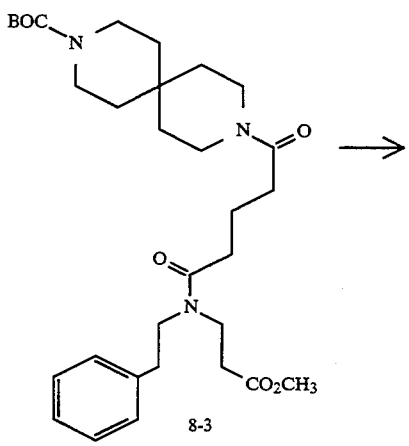

8-3

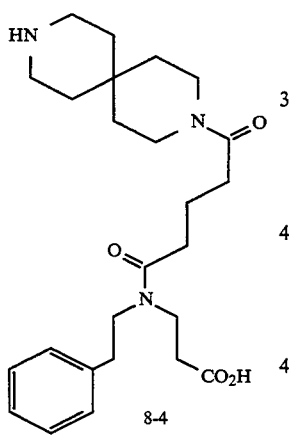

8-4

Step A:

415 mgs (2.0 mmol) N-(2-Phenethyl)-β-alanine 8-1 (*J. Pharmaceutical Sci. Vol.* 61, NO 11 p1739, 1972) was dissolved in DMF (2 mL) and treated with 8-2 (368 mgs, 1 mmol), HOBt (306 mgs), and EDC (248 mgs) and stirred for 15 hrs. The mixture was diluted with water and extracted with ethyl acetate and washed with 10% aqueous citric acid. The organic portions were washed with water, and 5% aqueous sodium bicarbonate and brine. The organics were dried (Na$_2$SO$_4$), concentrated and flash chromatographed (silica gel, ethyl acetate) to yield after concentration of the appropriate fractions 425 mgs (75%) of 8-3 as an oil.

The BOC aminoester 8-3 was deprotected in a similar manner to that described in Example 1, Step H.

NMR (300 MHz, d6 DMSO, partial): 2.17 (q, 2H) 2.45 (t, 2H) 3.00 (bs, 4H)7.18–7.35 (m, 5H).

EXAMPLE 9

3-{2-[(3-Azaspiro[5.5]undecane-9-carbonyl-)amino]acetylamino} propionic acid

Step A:

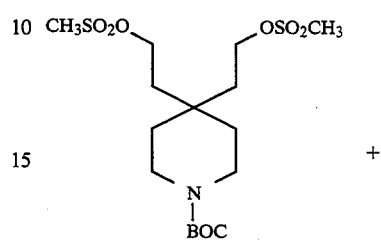

1-5

$CH_3CH_2OCOCH_2COOCH_2CH_3$ $\xrightarrow{\text{NaH}}{\text{Toluene}}$

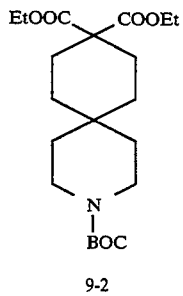

9-2

To a slurry of 60% NaH (2.04 g, 0.51 mole) in toluene (160 mL), under argon, was slowly added diethyl malonate (3.72 mL, 24.3 mmol). The mixture was cooled to 0° C. and the bis-mesylate 1-5 (7.0 g, 16.3 mmol) added as a solid and the mixture heated to reflux for 18 hours. The reaction was quenched into 10% citric acid (100 mL) and the product extracted with CH$_2$Cl$_2$ (2×150 mL). The extracts were dried (Na$_2$SO$_4$), concentrated to an oil, and chromatographed on silica to give 3.83 g (60%) of product 9-2.

$^1$H NMR (300 MHz, CDCl$_3$) δ: 1.22 (t, 6H), 1.4 (s, 9H), 2.0 (m, 4H), 3.35 (m, 4H), 4.2 (q, 4H).

Step B:

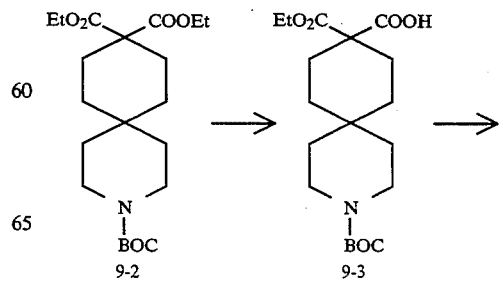

9-2   9-3

-continued

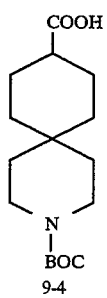
9-4

To a solution of the diester 9-2 (3.69 g, 0.0093 mol) in THF (50 mL) was added 1N LiOH (47 mL). The reaction was stirred for 3 days at 25° C., diluted with water (50 mL) and pH adjusted to 2.2 with KHSO₄. The product was extracted into ethyl acetate (2×75 mL), dried (Na₂SO₄), and concentrated to a foam (3.5 g). The solid was melted in a flask at 140° C. for 2 hours, cooled and the oil dissolved in THF (15 mL), 1N LiOH (10 mL) added and mixture stirred overnight at 30° C. The reaction was concentrated to remove THF, diluted with water (20 mL) and washed with diethyl ether (10 mL). The pH was adjusted to 2.5 with KHSO₄ and product extracted (3×50 mL) with ethyl acetate. The extracts were dried (Na₂SO₄), filtered and concentrated to a foam 9-4. Yield 2.48 g, 90%.

$^1$H NMR (300 MHz, CDCl₃, partial) δ: 1.45 (s, 9H), 3.4 (m, 4H).

Step C:

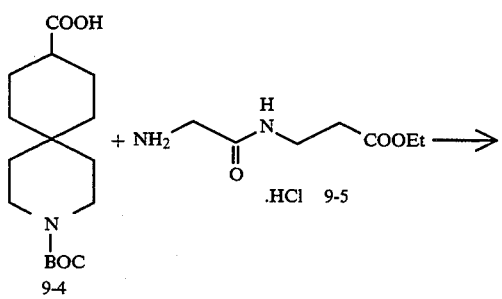

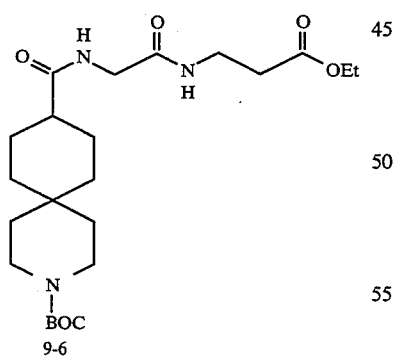
9-6

To a solution of the BOC-acid 9-4 (0.20 g) in DMF was added HOBt (0.118 g), diisopropylethylamine (0.130 mL), glycine-β-alanine ethyl ester.HCl-9-5 (0.141 g), followed by EDC (0.180 g). The mixture was stirred for 18 hours, diluted with water (20 mL) and extracted with ethyl acetate (3×20 mL). The ethyl acetate extracts were washed with 5% citric acid (2×15 mL), H₂O (10 mL), 5% sodium bicarbonate (2×15 mL) and brine (10 mL). The organic extracts were dried (Na₂SO₄), concentrated and chromatographed using 95% methylene chloride/methanol to give 0.252 g product 9-6. $^1$H NMR (300 MHz, CD₃OD, partial) δ: 3.0 (t, 3H), 1.4 (s, 9H), 2.5 (t, 2H), 6.2 (brs, 1H), 6.5 (brs, 1H).

Step D:

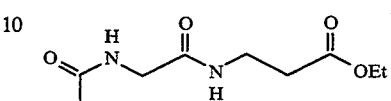

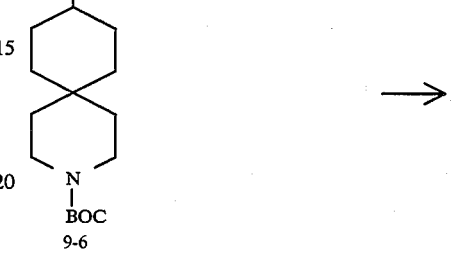
9-6

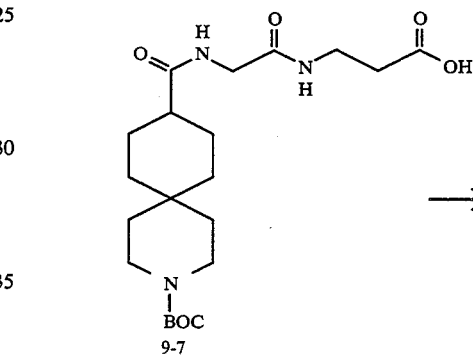
9-7

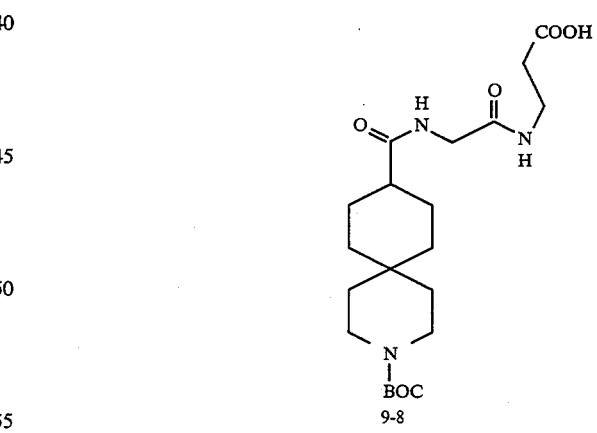
9-8

The BOC amino ester 9-6 was deprotected as described in Example 1, Step H to give the product 9-8.

$^1$H NMR (300 MHz, CD₃OD, partial) δ: 2.2 (m, 1H), 2.5 (t, 2H), 3.15 (m, 4H), 3.4 (t, 2H), 3.8 (s, 1H).

EXAMPLE 10

3-{3-[(3-Azaspiro[5.5]undecane-9-carbonyl)amino] propionylamino}propionic acid]propionic acid

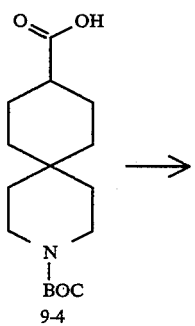

9-4

→

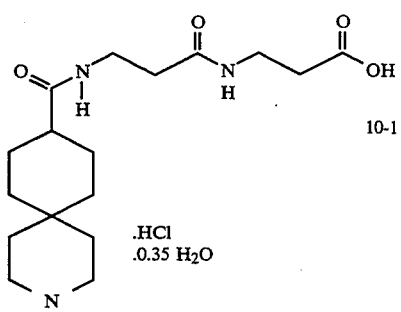

10-1

.HCl
.0.35 H₂O

3-{3-[(3-Azaspiro[5.5]undecane-9-carbonyl)amino]-propionylamino} propionic acid]propionic acid 10-1 was prepared in a similar manner to that described in Example 9.

CHN: Calc. C, 53.42; H, 8.10; N, 11.00 Found: C, 53.41; H, 7.84; N, 10.97

EXAMPLE 11

3-{3-[(3-Azaspiro[5.5]undecane-9-carbonyl)amino] propionylamino}-5-phenylpentanoic acid

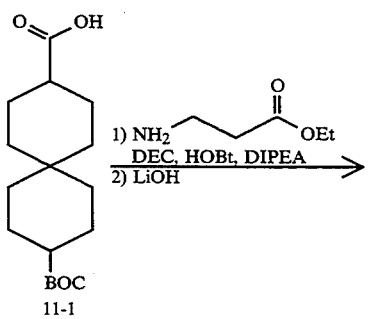

11-1

1) NH₂CH₂CH₂COOEt
   DEC, HOBt, DIPEA
2) LiOH

→

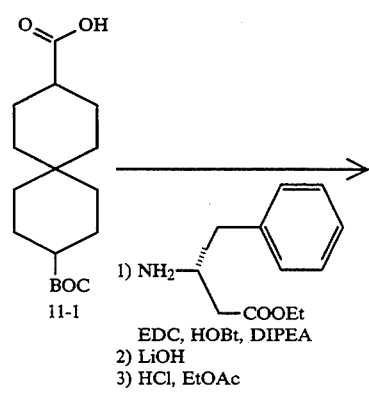

11-1

1) NH₂—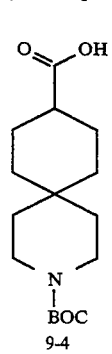—COOEt
   EDC, HOBt, DIPEA
2) LiOH
3) HCl, EtOAc

→

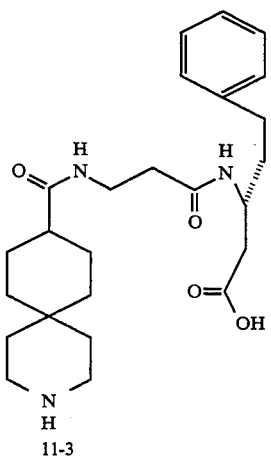

11-3

3-{3-[(3-Azaspiro[5.5]undecane-9-carbonyl)amino]-propionylamino}-5-phenylpentanoic acid 11-3 was prepared in a similar manner as described in Example 9.

¹H NMR (300 MHz, CD₃OD, partial) δ: 1.2–3.4 (brm, 29H), 4.2 (brm, 2H), 7.2 (brm, 5H), 7.9 (brs, 1H).

EXAMPLE 12

3-{2-(3-Azaspiro[5.5]undecane-9-carbonyl)amino]acetylamino}-5-phenylpentanoic acid

[structure with BOC 9-4]

→

[structure 12-1 with .HCl]

3-{2-(3-Azaspiro[5.5]undecane-9-carbonyl)amino]acetylamino}-5-phenylpentanoic acid 12-1 was prepared in a similar manner to that described in Example 9.

¹H NMR (300 MHz, CD₃OD, partial) δ: 1.25 (m, 2H), 2.5 (d, 2H), 4.2 (m, 2H), 7.2 (m, 5H), 7.92 (d, 1H), 8.15 (t, 1H).

EXAMPLE 13

3-[3-(3-Azaspiro[5.5]undecane-9-carbonyl)benzoylamino] propionic acid

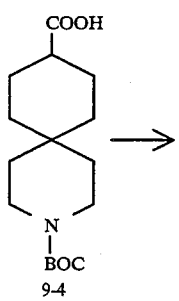
9-4

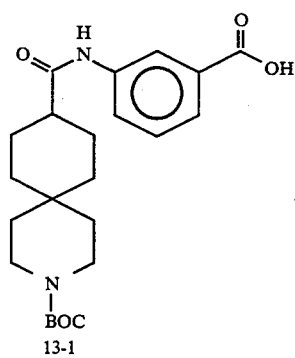
13-1

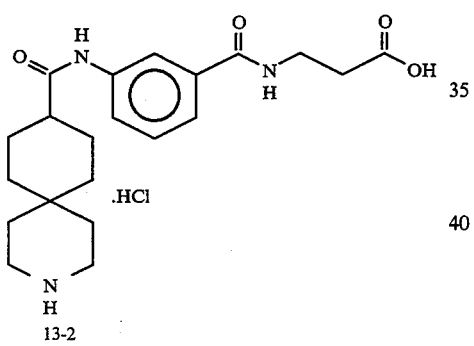
13-2

3-[3-(3-Azaspiro[5.5]undecane-9-carbonyl)benzoylamino]propionic acid 13-2 was prepared in a similar manner to that described in Example 9.

¹H NMR (300 MHz, CD₃OD, partial) δ: 2.4 (m, 1H), 2.65 (t, 3H), 3.6 (t, 2H), 7.2–8.0 (m, 4H), 9.9 (s, 1H).

EXAMPLE 14

3-[3-(3-Azaspiro[5.5]undecane-9-carbonyl)phenethylamino] propionic acid

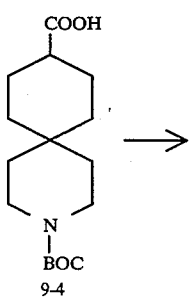
9-4

-continued

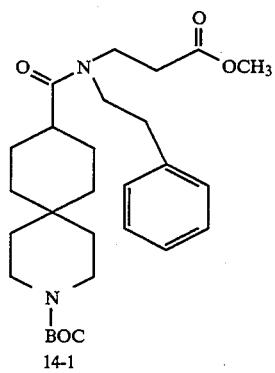
14-1

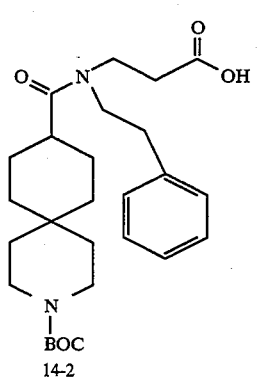
14-2

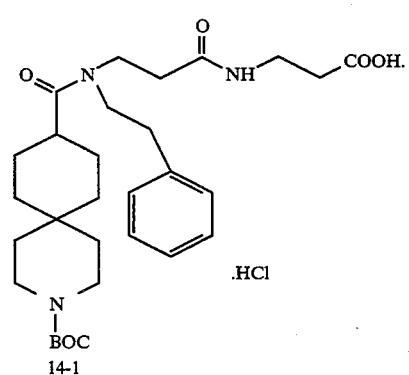
14-1

3-[3-(3-Azaspiro[5.5]undecane-9-carbonyl)phenethylamino]propionic acid 14-3 was prepared in a similar manner to that described in Example 9.

¹H NMR (300 MHz, CD₃OD) δ: 1.0–3.7 (m, 28H), 7.2–7.3 (m, 5H).

EXAMPLE 15

5-[3-(3-Azaspiro[5.5]undecane-9-carbonyl)phenyl]pentanoic acid

Step A:

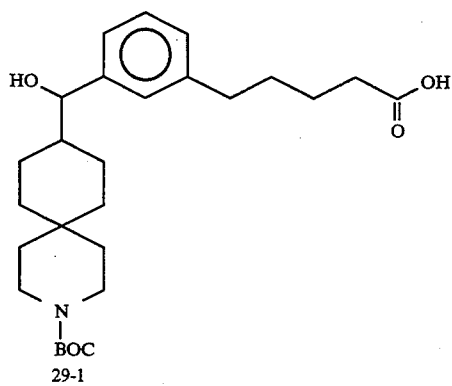

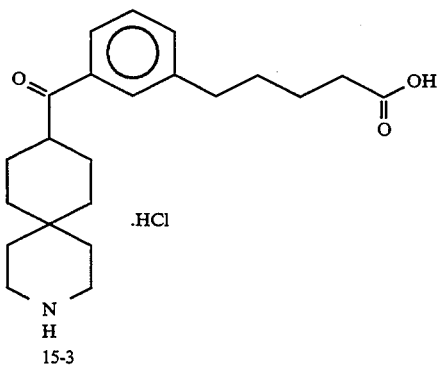

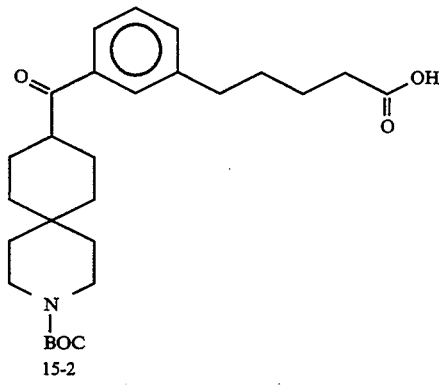

The BOC-alcohol acid 29-1, (0.24 g) (Example 29) was dissolved in DMF (8 mL) and pyridinium dichromate (50 mg) added. The reaction was allowed to stir and additional PDC added (100 mg) over a 12 hour period. The reaction was then quenched into Aq KHSO₄ (25 mL) and product extracted into ether (pH=2.0) (2×50 mL). The ether extracts were washed with aq. sodium sulfite, dried (Na₂SO₄) and concentrated to an oil. Column chromatography 95:5:1 (CH₂Cl₂/MeOH/AcOH) gave 170 mg of product 15-2.

$^1$H NMR (300 MHz, CDCl₃) δ: 1.45 (s, 9H), 2.38 (brt, 2H), 2.70 (brt, 2H), 3.25 (brm, 1H), 3.38 (m, 4H), 7.37 (m, 2H), 7.74 (m, 2H).

Step B:

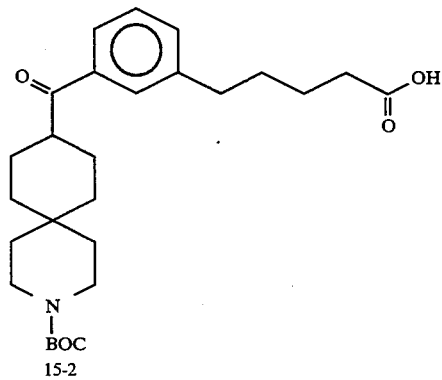

HCl gas was slowly bubbled into a 0° C. solution of the BOC-acid 15-2 (170 mg) in ethyl acetate over 1 hour. The reaction was concentrated to give a white solid which was flushed 2× with ethyl acetate (25 mL). The solid was stirred in ethyl acetate, filtered and dried in vacuo at 50° C. to give 134 mg of product 15-3. ©87

MP 196°–198° C. CHN: Calc. C, 67.07; H, 8.19; N, 3.56 Found: C, 66.09; H, 8.12; N, 3.74

EXAMPLE 16

3-(3-Azaspiro[5.5]undecane-9-carbonyl)benzoylamino propionic acid

Step A:

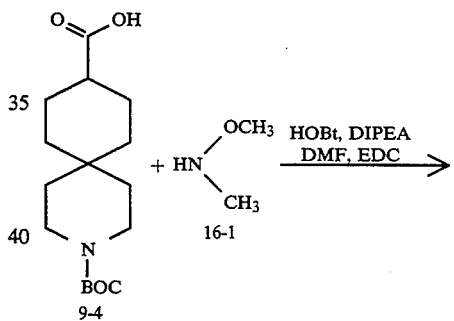

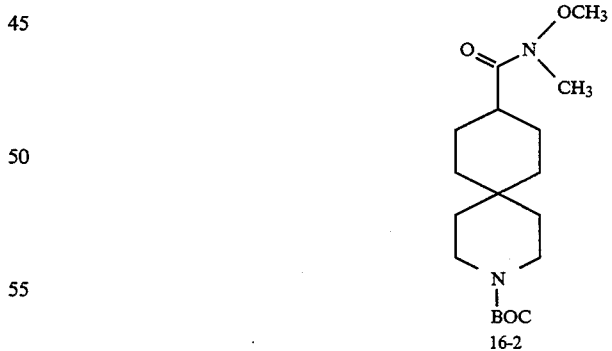

To a solution of the BOC-acid 9-4 (0.40 g), N,O-dimethylhydroxylamine hydrochloride 16-1 (0.134 gm), HOBt (0.236 g) and diisopropylethylamine (0.328 mL) in DMF (4 mL) was added EDC and the mixture stirred for 18 hours. The reaction was diluted with ethyl acetate (40 mL) and mixture washed with 5% citric acid (2×20 mL), H₂O (20 mL), 5% NaHCO₃ (2×20 mL) and sat NaCl (20 mL). The organic layer was dried (Na₂SO₄) and concentrated to a foam 16-2. Yield 0.452 g, 98%.

$^1$H NMR (300 MHz, CDCl$_3$) δ: 1.5 (s, 9H), 2.65 (brm, 1H), 3.2 (s, 3H), 3.4 (m, 4H), 3.7 (s, 3H).

Step B:

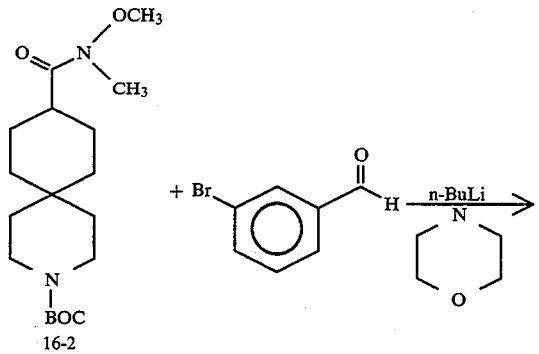

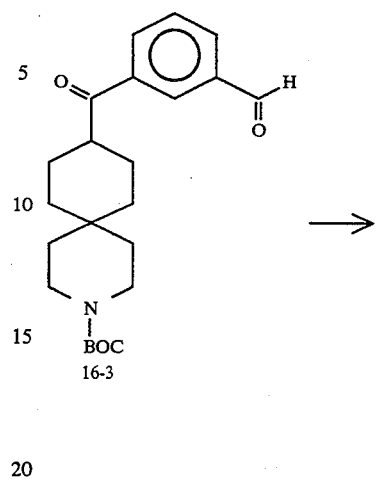

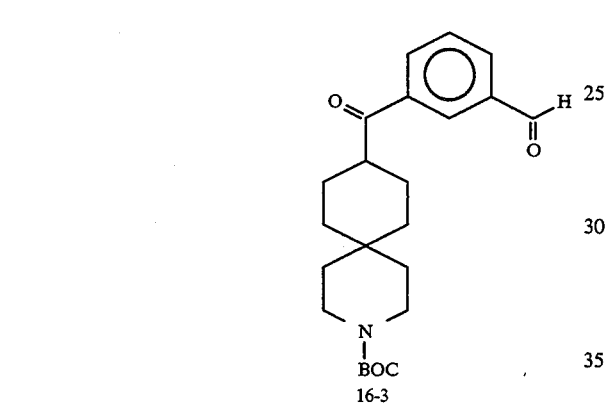

To a solution of THF (3 mL) containing morpholine (0.142 mL), at −78° C. under argon, was slowly added n-BuLi (0.637 mL). The reaction was stirred for 5 minutes after which a solution of m-bromobenzaldehyde (0.160 mL) in THF (2 mL) was slowly added. The reaction was stirred at −78° C. for 10 minutes and n-BuLi (0.531 mL) added slowly. The mixture was stirred at −78° C. for 30 minutes during which a thick precipitate formed. A solution of the BOC-amide 16-2 (0.452 g) in THF (5 mL) was then added, stirred at −78° C. for 15 minutes, and then allowed to warm to room temperature. After ½ hour at room temperature the reaction was quenched into aq. NaHSO$_4$ and product 16-3 extracted with ethyl acetate (3×40 mL). The organic extracts were dried (Na$_2$SO$_4$), concentrated and chromatographed on silica using ethyl acetate/hexane (90:10 to 70:30) to give 0.233 g product.

$^1$H NMR (300 MHz, CDCl$_3$) δ: 1.45 (s, 9H), 3.3 (m, 4H), 7.65 (t, 1H), 8.1 (d, 1H), 8.2 (d, 1H), 8.4 (s, 1H), 10.1 (s, 1H).

Step C:

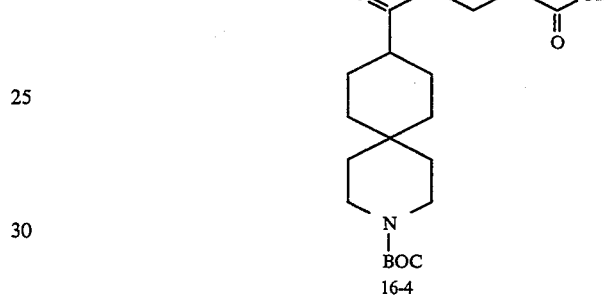

To a solution of the BOC aldehyde 16-3 (0.23 g) in methanol (2 mL) and acetonitrile (2 mL) was added 30% H$_2$O$_2$ (0.064 mL) followed by monosodium phosphate (0.20 g) in H$_2$O (0.5 mL). The mixture was stirred while sodium chlorite (0.096 g) was added. The reaction was stirred for 18 hours at room temperature, quenched with aq. sodium sulfite, pH adjusted to 2.5 with sodium hydrogen sulfate, and concentrated to remove solvents. The product 16-4 was extracted with ethyl acetate (2×25 mL), dried (Na$_2$SO$_4$) and concentrated to a foam. Yield 0.268 g, 100%.

$^1$H NMR (300 MHz, CDCl$_3$) δ: 1.5 (s, 9H), 1.7 (m, 4H), 3.4 (m, 4H), 7.6 (t, 1H), 8.2 (d, 1H), 8.3 (d, 1H), 8.65 (s, 1H).

Step D:

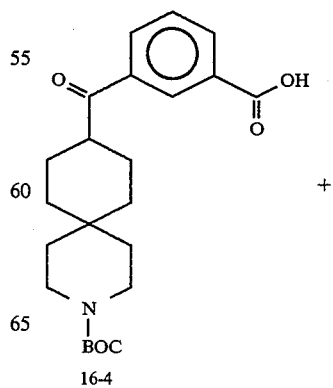

+

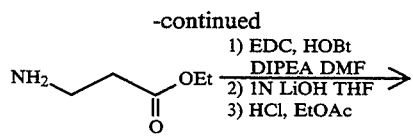

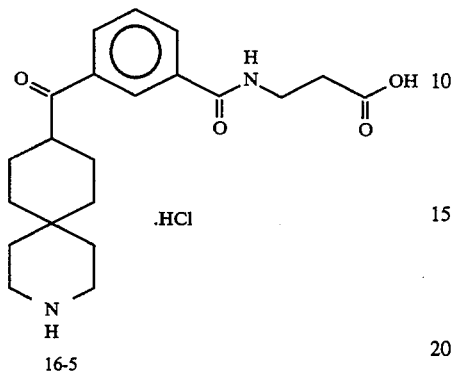

The BOC acid 16-4 and glycine ethyl ester hydrochloride were coupled and deprotected as described in Example 1, Steps G and H.

$^1$H NMR (300 MHz, CD$_3$OD) δ: 1.4–2.0 (m, 12H), 2.62 (t, 2H), 3.18 (m, 4H), 3.48 (m, 1H), 3.65 (t, 2H), 7.62 (t, 1H), 8.04 (d, 1H), 8.14 (d, 1H), 8.40 (s, 1H), 8.80 (m, 1H).

EXAMPLE 17

3-[3-(3-Azaspiro[5.5]undecane-9-carbonyl)benzoylamino]-2-(butanesulfonylamino)propionic acid

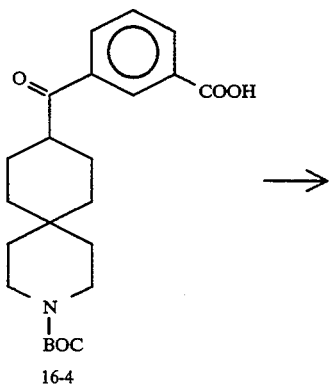

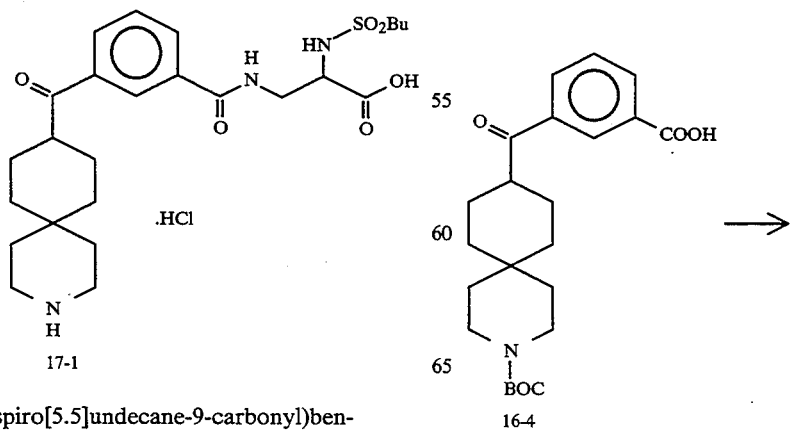

3-[3-(3-Azaspiro[5.5]undecane-9-carbonyl)benzoylamino]-2-(butanesulfonylamino)propionic acid 17-1 was prepared in a similar manner to that described in Example 16.

MP 155°–157° C.

EXAMPLE 18

3-[3-(3-Azaspiro[5.5]undecane-9-carbonyl)benzoylamino]butyric acid

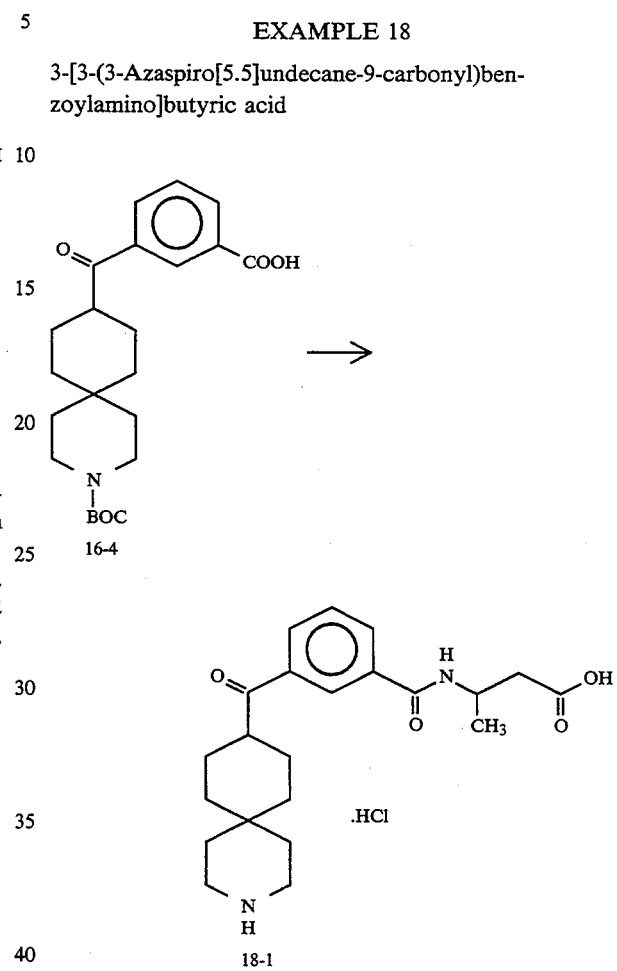

3-[3-(3-Azaspiro[5.5]undecane-9-carbonyl)benzoylamino]butyric acid 18-1 was prepared in a similar manner to that described in Example 16.

MP 145°–148° C.

EXAMPLE 19

1-[3-(3-Azaspiro[5.5]undecane-9-carbonyl)benzoyl]-piperidine-3-carboxylic acid

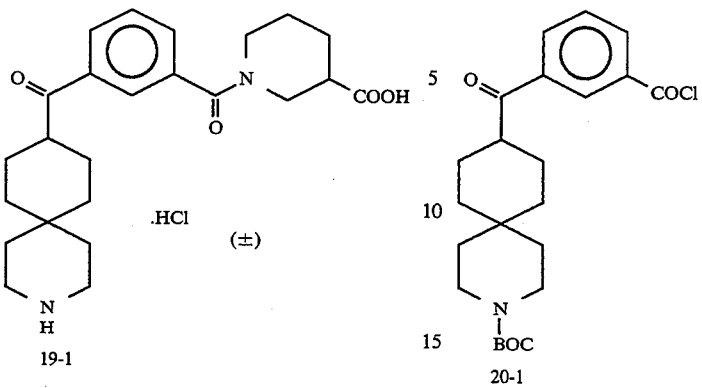

1-[3-(3-Azaspiro[5.5]undecane-9-carbonyl)benzoyl]-piperidine-3-carboxylic acid 19-1 was prepared in a similar manner to that described in Example 16.

MP 146°–148° C.

EXAMPLE 20

3-[3-(3-Azaspiro[5.5]undecane-9-carbonyl)ben-zoylamino]-N-(1-methoxycarbonyl-2-phenylethyl)succinamic acid and 3-[3-(3-Azaspiro[5.5]undecane-9-carbonyl)benzoylamino]-N-(1-carboxy-2-phenylethyl) succinamic acid Step A:

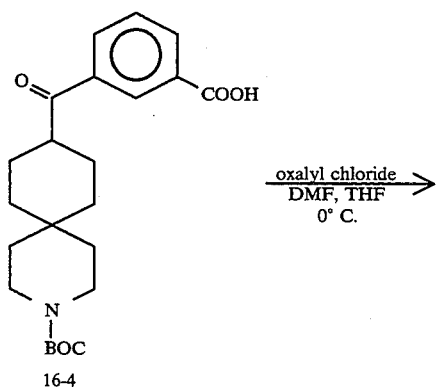

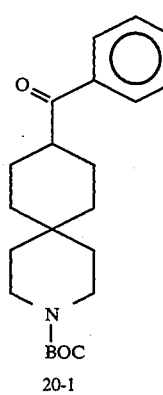

To a solution of the acid 16-4 (150 mg, 0.374 mmole) in THF (7 mL) at 0° C. was added DMF (1 drop) and oxalyl chloride (0.06 mL) and mixture stirred at 0° C. for 2½ hours. The reaction was concentrated to an oil at 0° C. and redissolved in THF (10 mL) for use.

Step B:

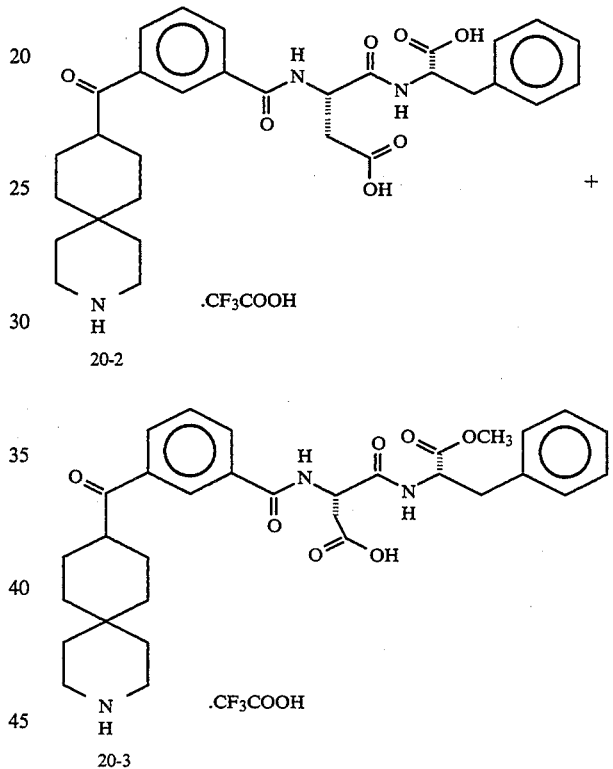

To a rapidly stirred mixture of L-Aspartyl-L-phenylalanine methyl ester (110 mg) in $H_2O$ (3 mL) and THF (3 mL) containing $K_2CO_3$ (74 mg) and 87% KOH (24 mg) at 0° C. was added a solution of 20-1 (150 mg) in THF (10 mL). The mixture was stirred for 15 minutes and then the pH was adjusted to 2.5 with aq. $KHSO_4$ and products extracted into ethyl acetate. The two products were chromatographed on silica using 95:5:1 ($CH_2Cl_2$/MeOH/Acetic acid) to give 90 mg of A and 85:15:1 eluent to give 85 mg B. Both A and B were treated with anhydrous HCl in ethyl acetate (20 mL) at 0° C., concentrated and prep HPLC purified using 0.1% $CF_3COOH/H_2O$, MeOH to give 35 mg 3-[3(3-Azaspiro[5.5]undecane-9-carbonyl)benzoylamino]-N-(1-methoxycarbonyl-2-phenylethyl)succinamic acid 20-3 from A and 5 mg 3-[3-(3-Azaspiro[5.5]undecane-9-carbonyl)benzoylamino]-N-(1-carboxy-2-phenylethyl) succinamic acid 20-2 from B.

MP 150°–155° C. MS 20-2: M+1-564, MP 20-3: 117°–119° C.

EXAMPLE 21

3-[3-(3-Azaspiro[5.5]undecane-9-carbonyl)benzenesulfanyl]propionic acid

Step A:

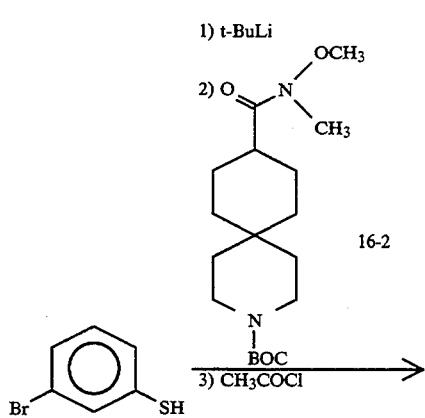

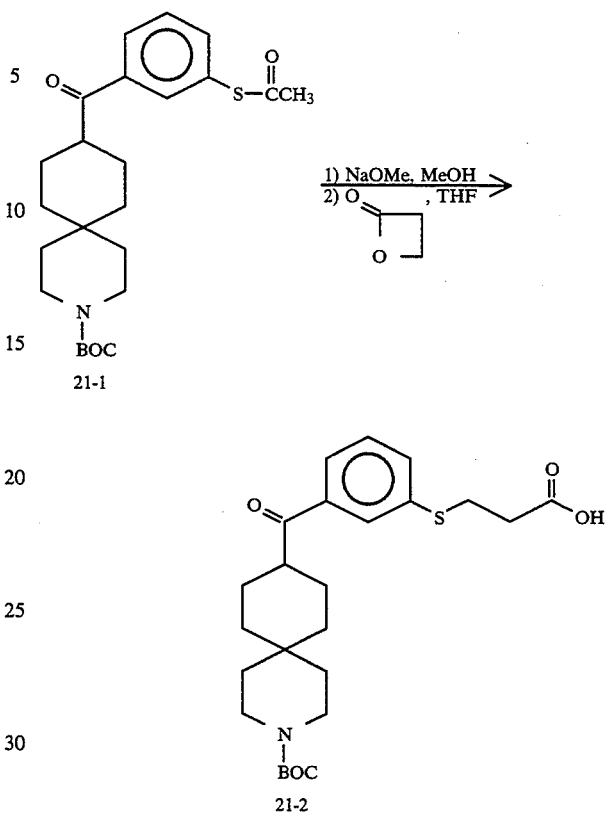

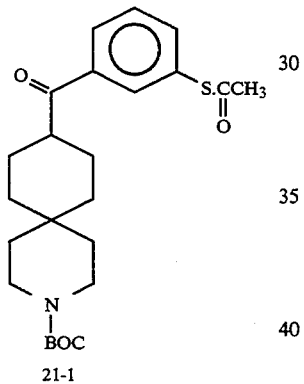

To a solution of m-bromothiophenol (1.51 g) in THF (40 mL) under argon and cooled to −78° C. was added 1.7M t-BuLi/pentane (9.4 mL). The yellow solution was stirred at −78° C. while a solution of the BOC-amide 16-2 (0.91 g) in THF (25 mL) was added. After stirring for 5 minutes, acetyl chloride (1.14 mL) was added and reaction aged at −50° C. for 15 minutes. The reaction was quenched into a solution of ethyl acetate (250 mL) and water (100 mL), stirred well and the organic layer removed. The aqueous layer was washed with ethyl acetate (2×75 mL). The organic extracts were combined, concentrated and chromatographed on silica using 20% ethyl acetate/hexane to give 0.85 g of product 21-1.

MS M+1—432.

Step B:

21-1 (0.40 g) was dissolved in argon degassed methanol (4 mL) and then treated with 0.826M NaOMe (1.18 mL). The yellow reaction was stirred at room temperature for 1 hour, concentrated to a solid dissolved in dry THF and reconcentrated to give a solid. The solid was redissolved in THF (10 mL), cooled to −10° C. and β-propiolactone (0.0777 mL) added. The reaction was stirred for 10 minutes, poured into ethyl acetate (125 mL) and water (75 mL), the pH adjusted to 2.5 with $KHSO_4$ and product extracted into ethyl acetate (2×50 mL). The organic extracts were dried over $Na_2SO_4$, filtered and concentrated to give 0.416 g product 21-2.

$^1H$ NMR (300 MHz, $CDCl_3$) δ: 1.40 (s, 9H), 2.68 (t, 2H), 3.18 (m, 1H), 3.20 (t, 2H), 3.36 (m, 4H), 7.42 (t, 1H), 7.54 (d, 1H), 7.76 (d, 1H), 7.92 (brs, 1H).

Step C:

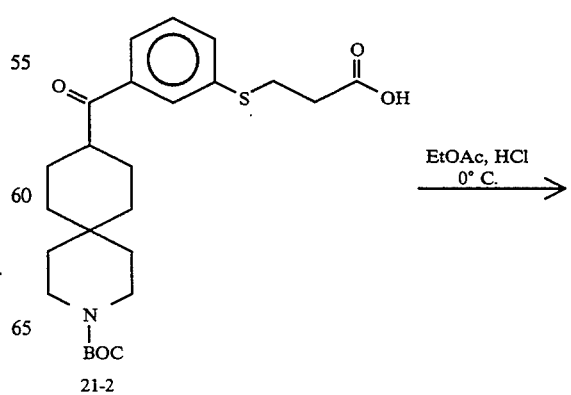

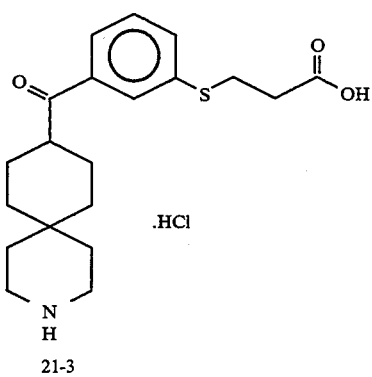

21-3

The BOC group was removed in a similar manner to that described in Example 1, Step H.

MP 196°–198° C. CHN: Calc. C, 67.07; H, 8.19; N, 3.56 Found: C, 66.09; H, 8.12; N, 3.74

EXAMPLE 22

3-[3-(3-Azaspiro[5.5]undecane-9-carbonyl)benzenesulfonyl] propionic acid

Step A:

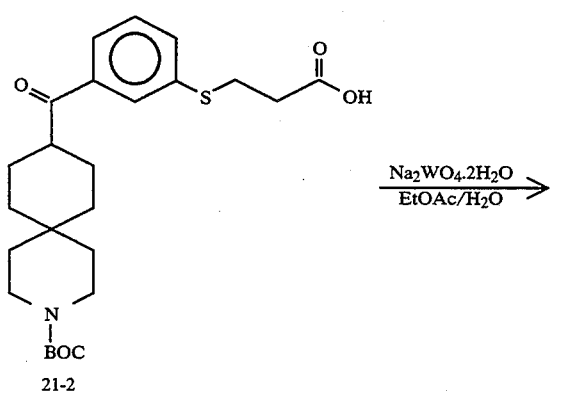

21-2

The BOC thio acid 21-2 (0.284 g) was dissolved in ethyl acetate (15 mL) and water (2 mL), and sodium tungstate dihydrate (30 mg) and 30% hydrogen peroxide (0.371 mL) added. The mixture was warmed to 40° C. and let stir for 48 hours. The reaction was cooled and product extracted into ethyl acetate, dried ($Na_2SO_4$) and concentrated to give 0.304 g product 22-1.

$^1$H NMR (300 MHz, $CDCl_3$) δ: 1.45 (s, 9H), 2.85 (t, 2H), 3.25 (m, 1H), 3.38 (m, 4H), 3.48 (t, 2H), 7.72 (t, 1H), 8.10 (d, 1H), 8.23 (d, 1H), 8.42 (s, 1H).

Step B:

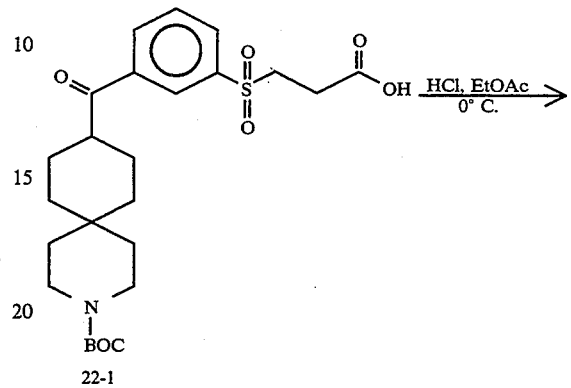

22-1

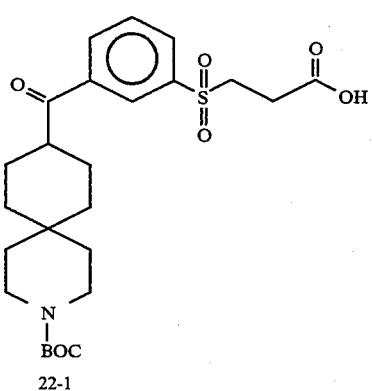

22-2

The BOC group was removed in a similar manner to that described in Example 1, Step H.

MP 165°–167° C. CHN: Calc. C, 55.87; H, 6.56; N, 3.26 Found: C, 55.62; H, 6.70; N, 3.46

EXAMPLE 23

3-[3-(3-Azaspiro[5.5]undecane-9-carbonyl)phenylsulfonylamino] propionic acid

Step A:

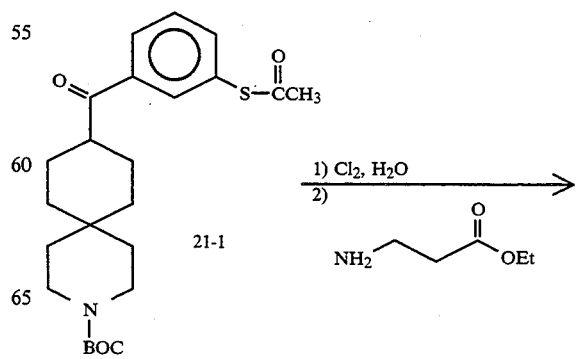

21-1

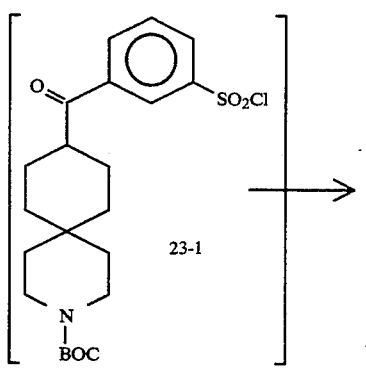

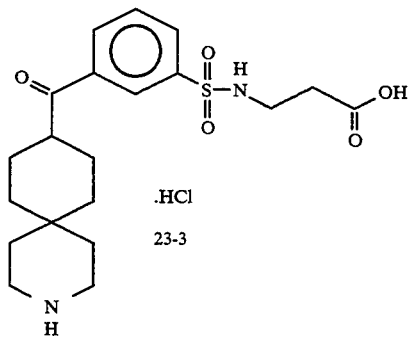

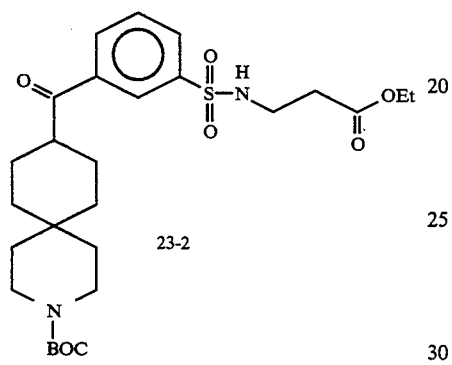

To a suspension of thioacetate (125 mg) in water (25 mL) at 0° C. was introduced chlorine gas over 15 minutes. The solid turned yellow but remained a suspension. The reaction was diluted with diethyl ether (20 mL) and product extracted into ether. The ether layer was removed, washed with aqueous sodium thiosulfate, dried (Na$_2$SO$_4$) and concentrated at <10° C. to an oil. The oil was redissolved in ethyl acetate (10 mL) and added to a mixture of β-alanine ethyl ester.HCl (50 mg) and triethylamine (45 μL). After stirring for 18 hours, the reaction was quenched with water (10 mL) and product extracted into ethyl acetate (40 mL). The organic extract was washed with 10% citric acid (10 mL), water (10 mL) and sat. NaHCO$_3$ (10 mL) to give, upon concentration, 155 mg of product 23-2.

$^1$H NMR (300 MHz, CDCl$_3$) δ: 1.25 (t, 3H), 1.48 (s, 9H), 2.57 (t, 2H), 3.24 (m, 4H), 3.40 (m, 1H), 4.12 (q, 2H), 5.35 (t, 1H), 7.65 (t, 1H), 8.05 (d, 1H), 8.14 (d, 1H), 8.38 (s, 1H).

Step B:

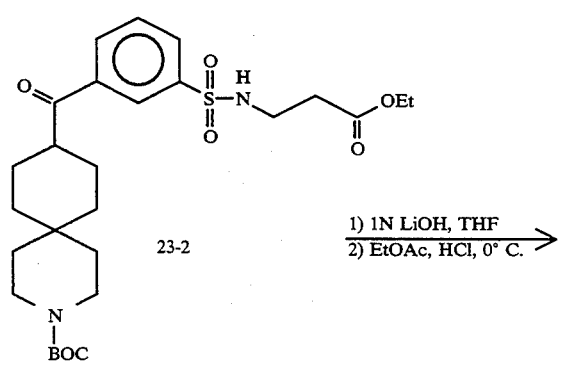

The BOC amino ester 23-2 was deprotected in a similar manner to that described in Example 1, Step H.

MP 170°–173° C. CHN: Calc. C, 53.99; H, 6.57; N, 6.30 Found: C, 53.84; H, 6.43; N, 6.34

EXAMPLE 24

[3-(3-Azaspiro[5.5]undecane-9-carbonyl)benzenesulfonyl]acetic acid

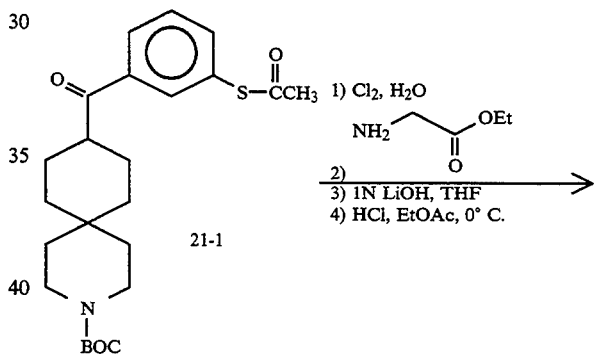

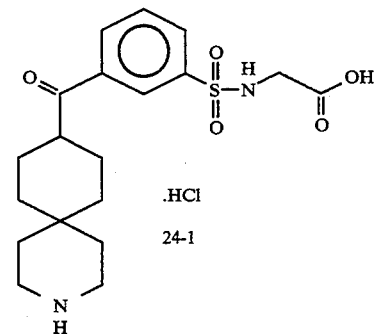

[3-(3-Azaspiro[5.5]undecane-9-carbonyl)benzenesulfonyl]acetic acid 24-1 was prepared in a similar manner to that described in Example 23.

MP 134°–138° C.

EXAMPLE 25

3-{[3-(3-Azaspiro[5.5]undecane-9-carbonyl)benzenesulfony] methylamino}propionic acid

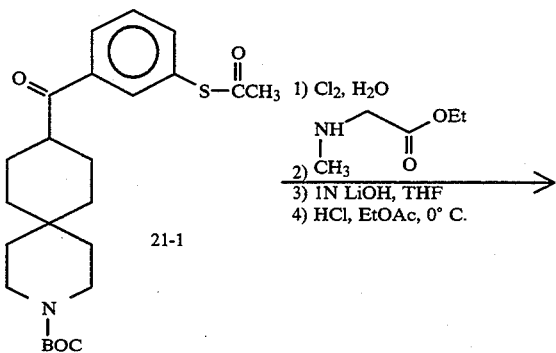

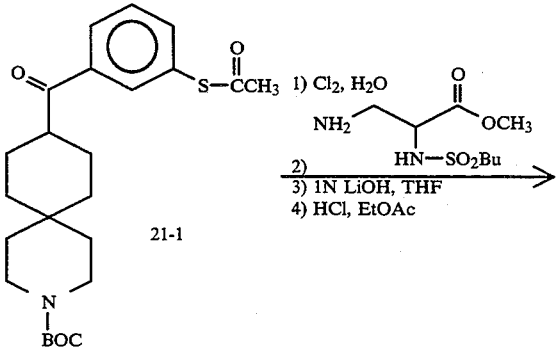

3-{[3-(3-Azaspiro[5.5]undecane-9-carbonyl)benzenesulfony]methylamino}propionic acid was prepared in a similar manner to that described in Example 23.
MP 224°–227° C.

EXAMPLE 26

3-[3-(3-Azaspiro[5.5]undecane-9-carbonyl)benzenesulfonyl-amino]-2-(butanesulfonylamino)propionic acid

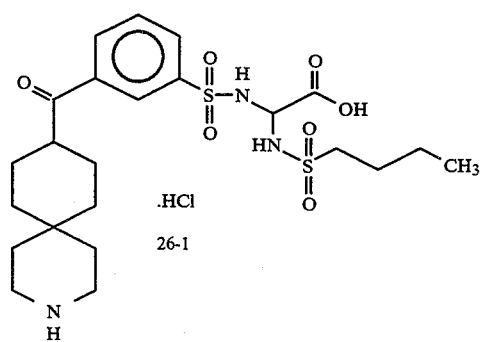

3-[3-(3-Azaspiro[5.5]undecane-9-carbonyl)benzenesulfonyl-amino]-2-(butanesulfonylamino)propionic acid 26-1 was prepared in a similar manner to that described in Example 23.

MP 225°–235° C. MS M+1—544

EXAMPLE 27

5-[3-(3-Azaspiro[5.5]undecane-9-carbonyl)phenyl]-5-hydroxypentanoic acid

Step A:

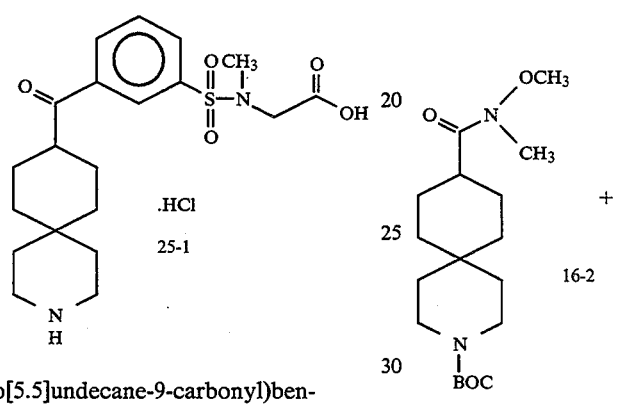

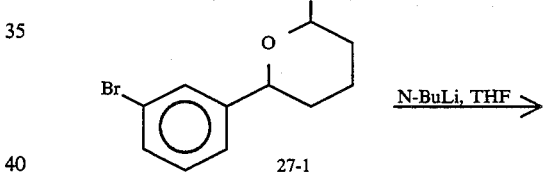

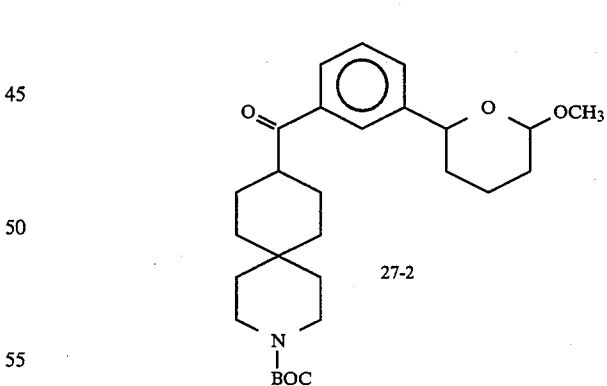

Compound 27-2 was prepared from the BOC amide 16-2 and methoxy bromide 27-1 using the procedure described in Example 16.

$^1$H NMR (300 MHz, CDCl$_3$) δ: 1.46 (s 9H), 3.3 (m, 1H), 4.52 (dd, 1H), 4.82 (dd, 1H), 4.90 (brs, 1H), 7.44 (t, 1H), 7.58 (d, 1H), 7.83 (d, 1H), 7.93 (s, 1H).

Step B:

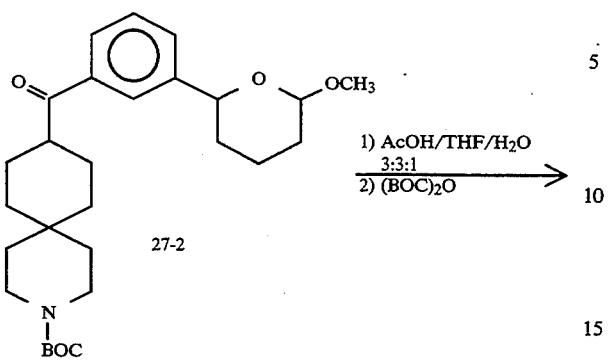

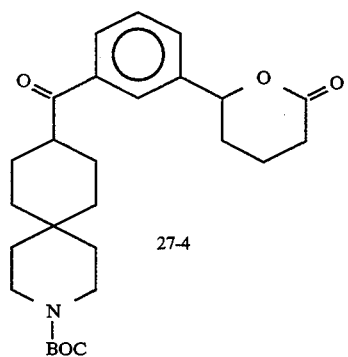

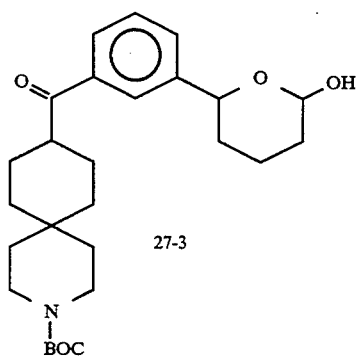

A solution of the BOC-methoxylactol 27-2 (1.5 g) in acetic acid/THF/H₂O (3:3:1, 47 mL) was warmed to 70° C. and aged for 28 hours. The reaction was concentrated and toluene added to residue. Concentration of this solution gave an oil which was dissolved in CH₂Cl₂ (20 mL), washed with water (10 mL) and 5% NaHCO₃, dried (Na₂SO₄) and concentrated to give an oil 27-3 (1.428 g).

¹H NMR (300 MHz, CDCl₃) δ: 1.25 (t, 2H), 1.46 (s, 9H), 3.25 (m, 1H), 3.38 (m, 4H), 4.58 (dd, 1H), 4.94 (dd, 1H), 5.08 (dd, 1H), 5.50 (brs, 1H), 7.44 (dt, 1H), 7.58 (dd, 1H), 7.83 (dd, 1H), 7.92 (s, 1H).

Step C:

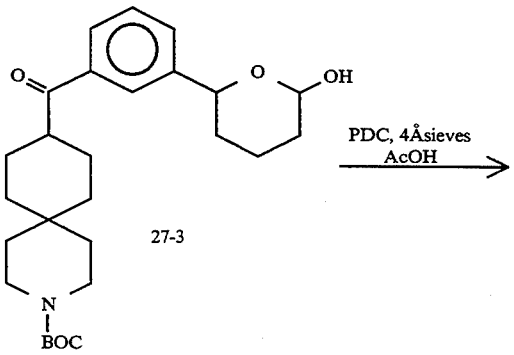

To a solution of the BOC-lactol 27-3 (0.1 g) in CH₂Cl₂ (1 mL) was added pyridinium dichromate (PDC) (0.123 g) and powdered anhydrous 4 Å molecular sieves. To this mixture was added acetic acid (21 ul) and reaction stirred for 30 minutes. The reaction mixture was poured onto a silica column and product 27-4 eluted with ethyl acetate/hexane to give 69 mg, 70%.

¹H NMR (300 MHz, CDCl₃) δ: 1.46 (s, 9H), 3.25 (m, 1H), 3.38 (m, 4H), 5.41 (dd, 1H), 7.49 (t, 1H), 7.57 (d, 1H), 7.90 (m, 2H).

Step D:

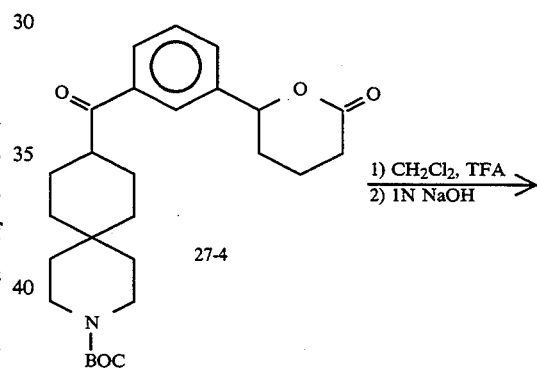

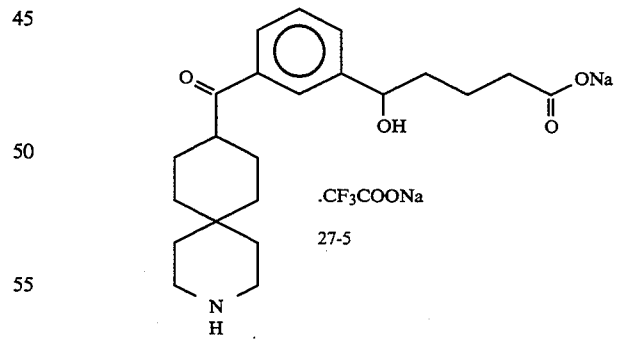

To a solution of the BOC lactone 27-4 (0.15 g) in CH₂Cl₂ (3 mL) at 0° C. was added trifluoroacetic acid (1 mL) and reaction stirred at 0° C. for 45 minutes. The reaction was concentrated in vacuo at 0° C. and residue passed through a prep HPLC C-18 column eluting with 0.1% CF₃COOH/H₂O:acetonitrile to give 138 mg. The solid was taken up in 0.1N NaOH (6.2 mL, 2.1 eq) and stirred for 10 minutes. The reaction mixture was filtered, frozen and lyophilized to give a white powder 27-5 150 mg.

MS M+1—396 1H NMR (DMSO) δ: 1.2–1.8 (m, 18H), 2.0 (t, 2H), 3.40 (m, 1H), 4.60 (brt, 1H), 7.45 (t, 1H), 7.55 (d, 1H), 7.80 (d, 1H), 7.91 (s, 1H).

EXAMPLE 28

5-[3-(3-Azaspiro[5.5]undecane-9-carbonyl)phenyl]-5-oxopentanoic acid

Step A:

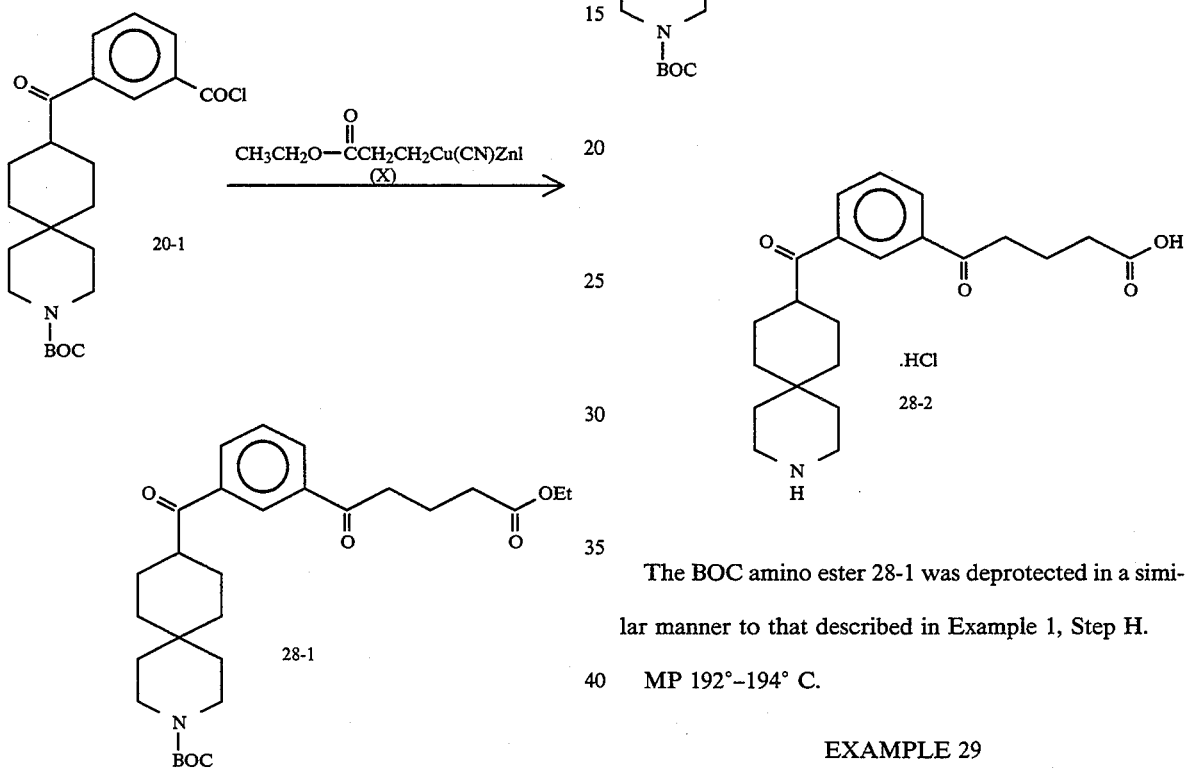

Ref. *JOC* 1988, 53, 2392–2394 for ZnCu reagent (X).

To the prepared copper reagent (X)(1 eg) in THF at −25° C. under argon was added the acid chloride 20-1 (150 mg) (Example 20) in THF (10 mL). The reaction was quenched into aq. NaHSO4/EtOAc and stirred for 10 minutes. The resulting solids were filtered and the mixture extracted with ethyl acetate (100 mL). The extracts were combined, washed with water (20 mL), 5% citric acid (20 mL) and 5% NaHCO3 (20 mL). The organic layer was concentrated to an oil and chromatographed on silica (60:40 Hexane/EtOAc) to give 74 mg product 28-1.

1H NMR (300 MHz, CDCl3) δ: 1.25 (t, 3H), 1.48 (s, 9H), 2.43 (t, 2H), 3.10 (t, 2H), 4.15 (q, 2H), 4.65 (m, 1H), 7.58 (t, 1H), 8.14 (t, 2H), 8.50 (s, 1H).

Step B:

The BOC amino ester 28-1 was deprotected in a similar manner to that described in Example 1, Step H.

MP 192°–194° C.

EXAMPLE 29

5-[3-(3-Azaspiro[5.5]undecane-9-carbonyl)phenyl]-2-(butanesulfonylamino)pentanoic acid Step A:

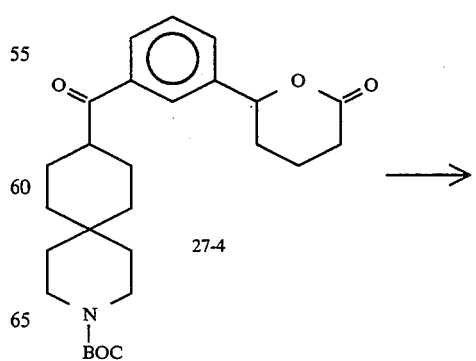

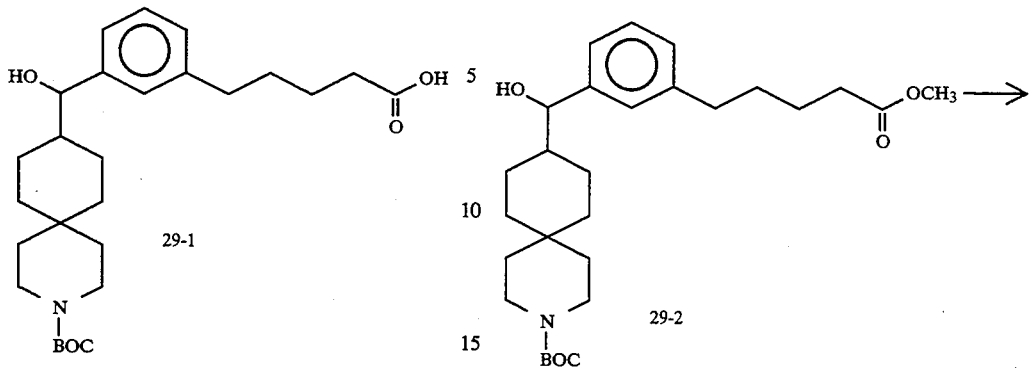

The BOC lactone 27-4 (1.0 g) (Example 27) was hydrogenated (1 atm.) in methanol (50 mL) and THF (50 mL) over 10% Pd/c (0.33 g) for 2 hours. The reaction was filtered and concentrated to a white foam, yield 1.0 g.

$^1$H NMR (300 MHz, CDCl$_3$) δ: 1.40 (s, 9H), 2.38 (m, 2H), 2.64 (m, 2H), 3.32 (m, 4H), 4.38 (d, 1H), 7.0–7.4 (m, 4H).

Step B:

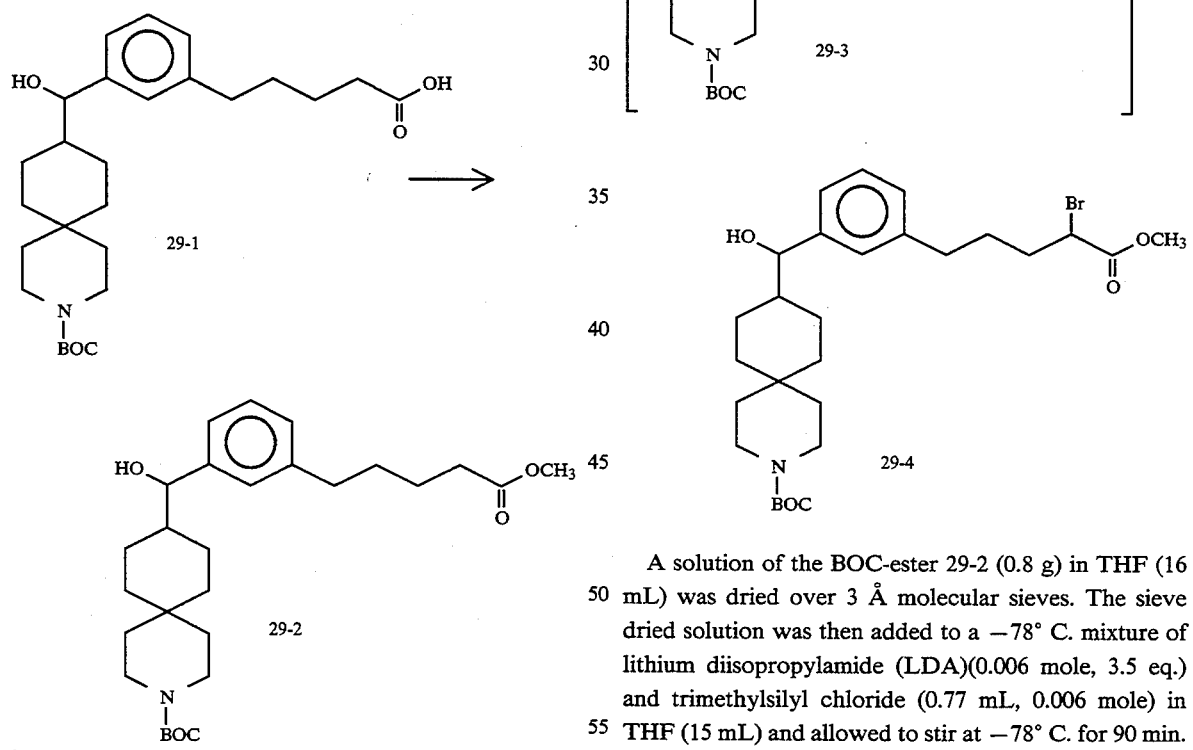

The BOC alcohol 29-1 was dissolved in 25 mL of 75% toluene/methanol, cooled to 0° C. and treated with a solution of 10% trimethylsilyl dizaomethane in hexane until complete reaction had occured as judged by TLC. The reaction mixture was then concentrated, diluted with toluene (25 mL) and reconcentrated to give an oil 29-2 (1.0 g).

$^1$H NMR (300 MHz, CDCl$_3$) δ: 1.42 (s, 9H), 2.54 (t, 2H), 2.62 (t, 2H), 3.34 (m, 4H), 3.66 (s, 3H), 4.36 (d, 1H), 7.0–7.4 (m, 4H).

Step C:

A solution of the BOC-ester 29-2 (0.8 g) in THF (16 mL) was dried over 3 Å molecular sieves. The sieve dried solution was then added to a −78° C. mixture of lithium diisopropylamide (LDA)(0.006 mole, 3.5 eq.) and trimethylsilyl chloride (0.77 mL, 0.006 mole) in THF (15 mL) and allowed to stir at −78° C. for 90 min. N-bromosuccinimide (0.36 g) was then added and the mixture allowed to warm to room temperature and react over 2 hours. The reaction was then quenched by addition of 1N HCl (pH≦2.0) and product extracted into ethyl acetate. Concentration of the extracts gave an oil, 29-4 (0.90 gm).

$^1$H NMR (300 MHz, CDCl$_3$) δ: 1.42 (s, 9H), 2.65 (t, 2H), 3.35 (m, 4H), 3.79 (s, 3H), 4.24 (dt, 1H), 4.38 (d, 1H), 7.0–7.4 (m, 4H).

Step D:

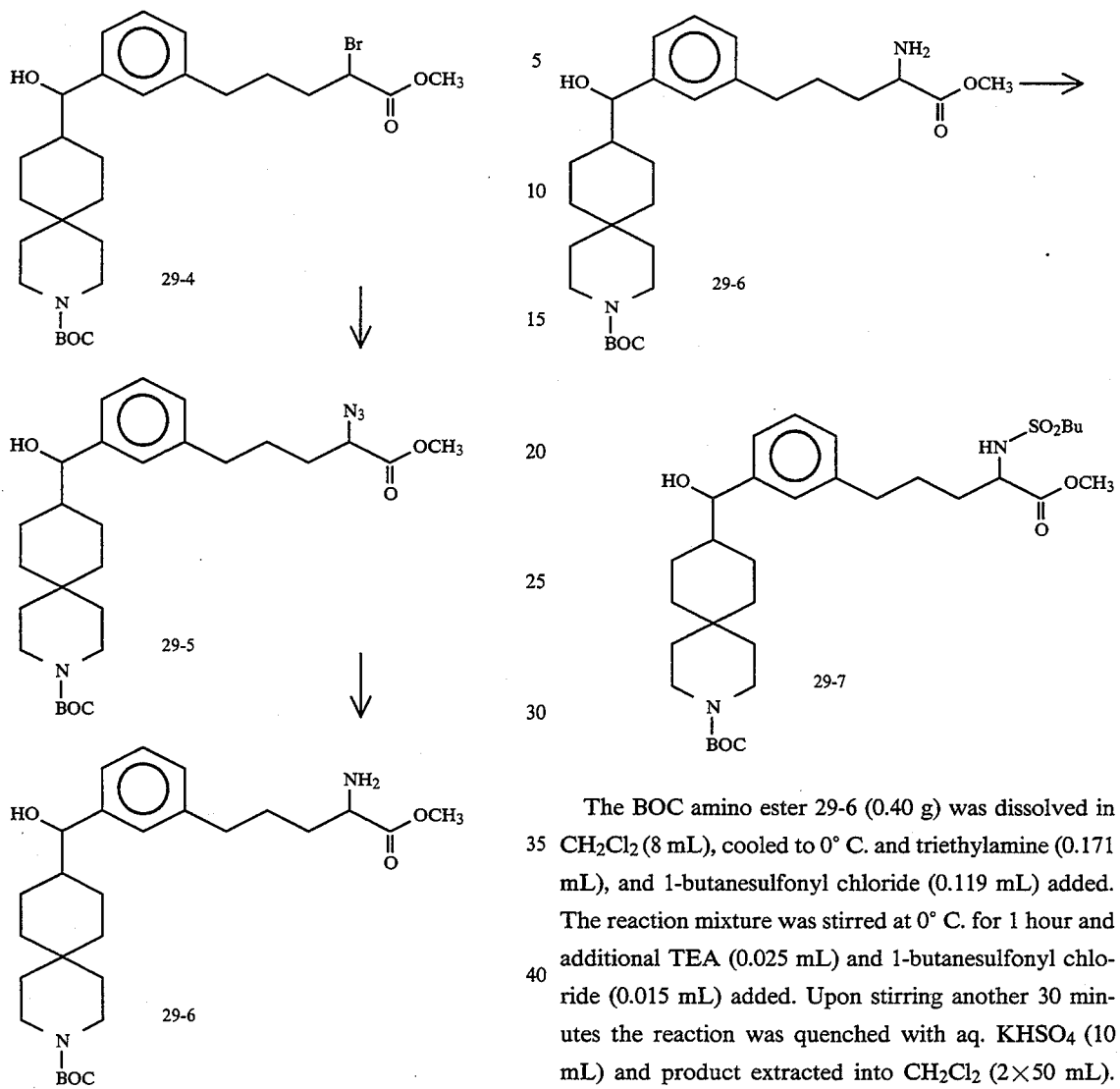

The BOC-bromide 29-4 (0.9 g) was dissolved in DMF (35 mL), NaN₃ (0.30 g) added and mixture allowed to stir overnite at 25° C. The reaction was diluted with Aq KHSO₄ (100 mL) and product extracted (pH=2.0) into ethyl acetate (2×150 mL). The organic extracts were washed with water (3×75 mL) and brine (50 mL), dried over Na₂SO₄ and concentrated to an oil. The oil was redissolved in ethyl acetate (100 mL) and hydrogenated 1 atm over 10% Pt/C (0.34 g) overnight (18 hours). Additional 10% Pt/C (0.25 g) was added and mixture hydrogenated another 4 hours till complete. The reaction was filtered and concentrated to give 0.6 g product 29-6.

$^1$H NMR (300 MHz, CDCl₃) δ: 1.42 (s, 9H), 2.65 (brs, 2H), 3.30 (brs, 4H), 3.74 (s, 3H), 4.34 (d, 1H), 7.0–7.3 (m, 4H).

Step E:

The BOC amino ester 29-6 (0.40 g) was dissolved in CH₂Cl₂ (8 mL), cooled to 0° C. and triethylamine (0.171 mL), and 1-butanesulfonyl chloride (0.119 mL) added. The reaction mixture was stirred at 0° C. for 1 hour and additional TEA (0.025 mL) and 1-butanesulfonyl chloride (0.015 mL) added. Upon stirring another 30 minutes the reaction was quenched with aq. KHSO₄ (10 mL) and product extracted into CH₂Cl₂ (2×50 mL). The extracts were dried (Na₂SO₄), and concentrated to give 0.484 g product 29-7.

1H NMR (300 MHz, CDCl₃) δ: 0.95 (t, 3H), 1.42 (s, 9H), 3.30 (s, 3H), 3.40 (m, 4H), 7.0–7.3 (m, 4H).

Step F:

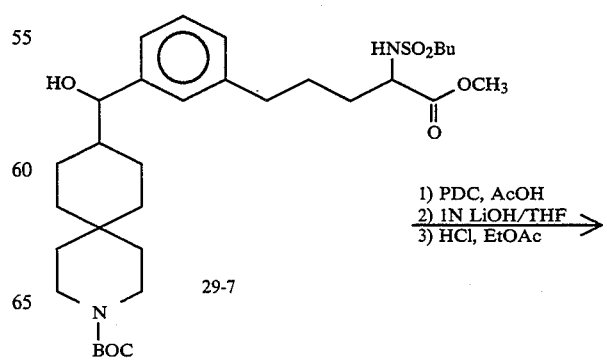

1) PDC, AcOH
2) 1N LiOH/THF
3) HCl, EtOAc

-continued

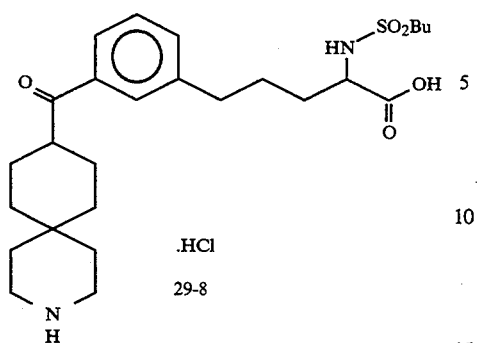

29-8

The Boc-alcohol ester 29-7 was oxidized using PDC as described in Example 15 then deprotected as described in Example 1, Step H.
MP 130°–135° MS M+1—493

EXAMPLE 30

7-(3-Azaspiro[5.5]undec-3-yl)-8-oxooctanoic acid

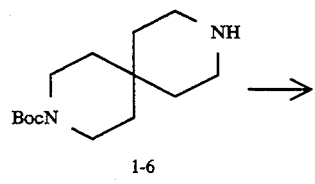

1-6

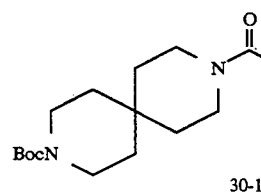

30-1

At room temperature under an atmosphere of argon, the amine 1-6 (150 mg, 0.59 mmol), hydroxybenzotriazole monohydrate (181 mg, 1.18 mmol), 1-ethyl-3-[3-(dimethylamino)propyl]carbodiimide hydrochloride (226 mg, 1.18 mmol) and suberic acid, monomethyl ester (222 mg, 1.18 mmol) were combined in dimethylformamide (2 mL) and aged 18 h. The reaction mixture was partitioned between cold 1-M citric acid and ethyl acetate (15 mL each). The organics were washed with water (10 mL), sat. NaHCO3 (10 mL) and brine (10 mL) and dried over magnesium sulfate. The volatiles were removed under reduced pressure leaving a pale yellow oil which was purified by flash column chromatography (230–400 mesh silica, 1:1 EtOAc:Hex) to give 98 mg of the desired product 30-1 (40%).

H$^1$NMR (300 MHz, CDCl$_3$) δ: 3.59 (s, 3H), 3.50 (bs, 2H), 3.33 (bs, 6H), 2.26–2.21 (m, 4H), 1.58–1.53 (m, 4H), 1.38 (bs, 17H), 1.29–1.25 (m, 4H).

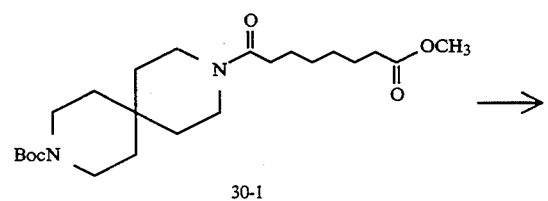

30-1

-continued

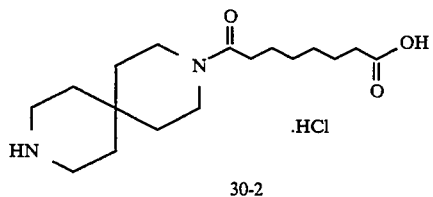

30-2

Deprotection of the Boc ester 30-1 as described for Example 1, Step H gave the title compound as a white hygroscopic foam, 30-2 in quantitative yields.

H$^1$NMR (300 MHz, D$_2$O) δ: 3.40 (bs, 4H), 3.05 (bs, 4H), 2.60–2.20 (m, 4H), 1.60 (bs, 4H), 1.40 (bs, 8H), 1.20 (bs, 4H).

EXAMPLE 31

8-(3-Azaspiro[5.5]undec-3-yl)-9-oxononanoic acid octanoic acid

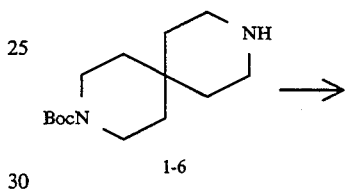

1-6

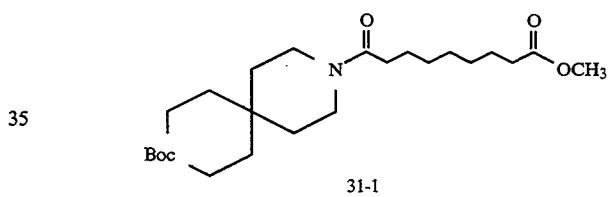

31-1

At room temperature under an atmosphere of argon, Boc amine 1-6 (150 mg, 0.59 mmol), hydroxybenzotriazole monohydrate (181 mg, 1.18 mmol), 1-ethyl-3-[3-(dimethylamino)propyl]carbodiimide hydrochloride (226 mg, 1.18 mmol) and azelaic acid, monomethyl ester (239 mg, 1.18 mmol) were combined in dimethylformamide (2 mL) and aged 18 h. The reaction mixture was partitioned between cold 1-M citric acid and ethyl acetate (15 mL each). The organics were washed with water (10 mL), sat. NaHCO3 (10 mL) and brine (10 mL) and dried over magnesium sulfate. The volatiles were removed under reduced pressure leaving a colorless oil which was purified by flash column chromatography (230–400 mesh silica, 1:1 EtOAc:Hex) to give 119 mg of the desired product 31-1 (46%).

H$^1$ NMR (300 MHz, CDCl$_3$) δ: 3.59 (s, 3H), 3.49 (bs, 2H), 3.33 (bs, 6H), 2.26–2.19 (m, 4H), 1.59–1.52 (m, 4H), 1.38 (bs. 17H), 1.25 (bs, 6H).

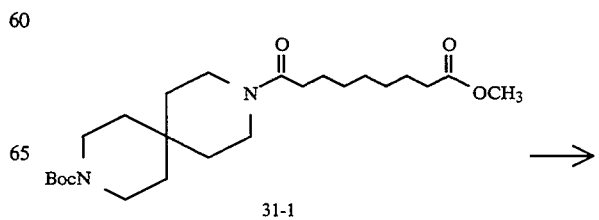

31-1

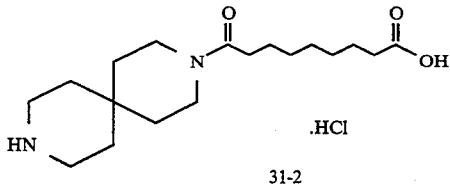

31-2

Deprotection of the Boc esters 31-1 as described in Example 1, Step H gave the title compound as a white hygroscopic foam in an 83% yield.

H¹ NMR (300 MHz, CD₃OD) δ: 3.60–3.45 (m, 4H), 3.30 (bs, 4H), 3.20 (bs, 4H), 2.40 (t, J=7.2 Hz, 2H), 2.30 (t, J=7.2 Hz, 2H), 1.80–1.70 (m, 4H), 1.65–1.50 (m, 8H), 1.40–1.35 (m, 4H).

EXAMPLE 32

7-[(3,9-Diazapiro[5.5]undecane-3-carbonyl)amino]heptanoic acid

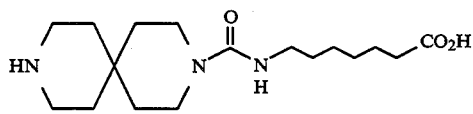

Step A:

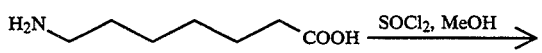

7-Aminoheptanoic acid (6.90 mmol, 1.00 g) and 50 mL methanol were combined in a 100 mL round bottom flask. The contents of the reaction flask were cooled in an ice bath under argon. Thionyl chloride (27.6 retool, 2.01 mL) was added dropwise via an addition funnel. A colorless solution resulted. Warmed to room temperature. After 30 min., the contents of the reaction flask were heated to reflux for 12 h. Solvent was removed from the reaction flask by rotory evaporation, then ether was added. A white solid appeared. The solid was isolated by vacuum filtration. 32-1 (1.11 g, 82.1%).

¹H NMR (300 MHz, DMSO-d₆) δ: 8.00–7.80 (s, br, 2H), 3.57 (s, 3H), 2.71 (m, 2H), 2.29 (t, J=7.32 Hz, 2H), 1.52 (m, 4H), 1.28 (m, 4H).

Step B:

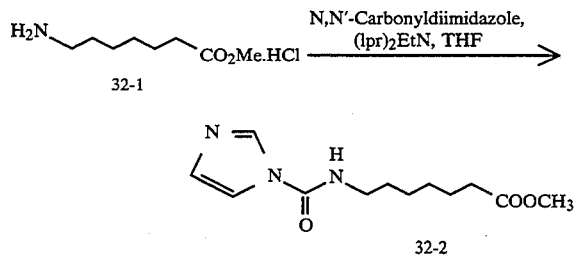

N,N'-Carbonyldiimidazole (972 mg, 6.00 mmol) and THF (20 ml) were combined in a 250 mL round bottom flask. The reaction flask was cooled in an ice/salt under argon. A suspension of the amino ester 32-1 (1.11 g, 5.69 mmol), diisopropylethylamine (989 μL, 5.69 mmol), and THF (10 mL) was placed in an addition funnel then added dropwise to the contents of the reaction flask. A colorless solution resulted. The reaction flask was cooled in a freezer for 24 h. Solvent was removed by rotory evaporation. A colorless oil remained. It was subjected to flash column chromatography using silica (EM Science, 230–400 mesh, 5×18 cm). The column was eluted with an ethyl acetate, hexane gradient. Fractions containing product were pooled then rotory evaporated to a colorless oil 32-2 (1.17 g, 81.5%).

¹H NMR (300 MHz, CDCl₃) δ: 8.18 (s, 1H), 7.43 (s, 1H), 7.06 (s, 1H), 6.76–6.68 (s, br, 1H), 3.67 (s, 3H), 3.43 (m, 2H), 2.33 (t, J=7.32 Hz, 2H), 1.64 (m, 4H), 1.39 (m, 4H).

Step C:

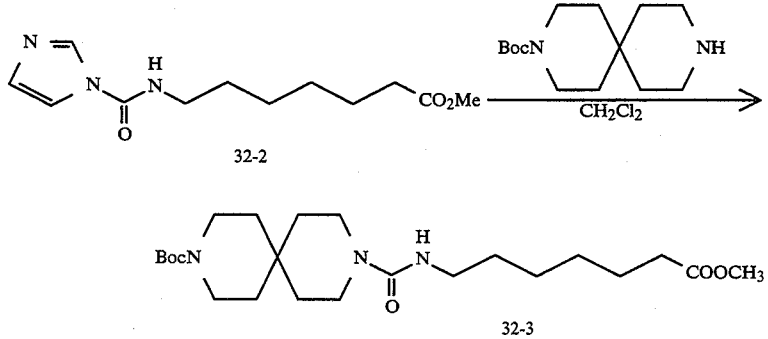

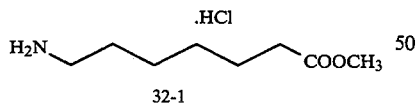

The Boc amine 32-2 (169 mg, 0.667 mmol), acyl imidazole (113 mg, 0.445 mmol), and chloroform (10 mL) were combined and heated to reflux for 60 min., then cooled to room temperature. Solvent was removed by rotory evaporation. A colorless oil resulted. It was subjected to flash column chromatography using silica (EM Science, 230–400 mesh/3×15 cm). The column was eluted with methylene chloride: methanol, 97:3. Fractions containing product were pooled, then rotory evaporated. A nearly colorless oil 32-3 remained (184 mg, 64.9%).

¹H NMR (300 MHz, CDCl₃) δ: 4.43 (s, br, 1H), 3.67 (s, 3H), 3.39 (m, 8H), 3.33 (m, 2H), 2.31 (t, J=7.32 Hz, 2H), 1.61 (m, 3H), 1.46 (m, 18H), 1.34 (m, 4H).

Step D:

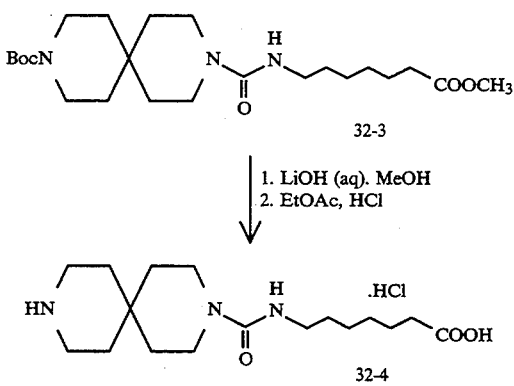

32-3

1. LiOH (aq). MeOH
2. EtOAc, HCl

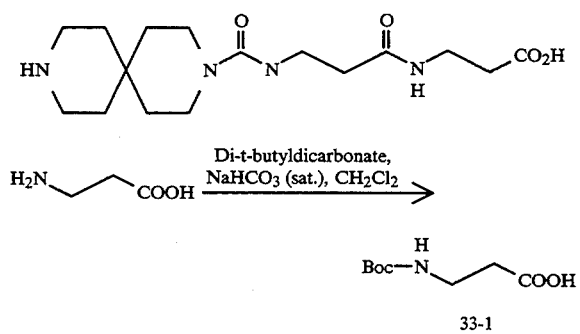

32-4

The Boc amino ester 32-3 was deprotected as described in Example 1, Step H.

Melting point: 178°-183° C. Elemental analysis: Calculated for $C_{17}H_{31}N_3O_3 \cdot HCl \cdot 0.55\ H_2O \cdot 0.30$ EtOAc (M.W. solvate: 398.26 g/mol) C, 54.88%; H 8.99%; N, 10.55%. Found: C, 54.84%; H, 8.88%; N, 10.52%.

$^1$H NMR (300 MHz, DMSO-d6) δ: 8.70 (s, br, 1H), 6.40 (s, br, 1H), 3.22 (m, 4H), 2.98 (m, 7H), 2.17 (t, J=7.33 Hz, 2H), 1.57 (t, br, 4H), 1.44 (m, 2H), 1.32 (m, 6H), 1.26–1.18 (m, 5H).

EXAMPLE 33

3-{3-[(3,9-Diazaspiro[5.5]undecane-3-carbonyl)amino]-propionylamino}propionic acid Step A:

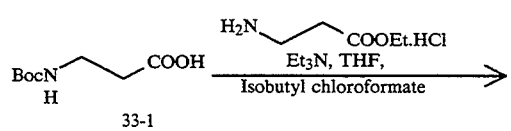

β-Alanine (3.00 g, 33.7 mmol) di-t-butyldicarbonate (8.00 g, 37.0 mmol), saturated sodium bicarbonate (10 mL), and ethyl acetate (100 mL) were combined and heated at 50° C. for 5 h., then heated to reflux for 1.5 h. The organic and aqueous layers were separated, and the aqueous layer was made acidic with citric acid and extracted with ethyl acetate (3×30 mL). The organic phases were dried (sodium sulfate) and the solvent evaporated. A white solid 33-1 formed (5.82 g, 91.4%).

$^1$H NMR (CDCl$_3$) δ: 5.20–5.00 (s, br, 1H), 3.44–3.34 (d, br, 2H), 2.64–2.54 (m, br, 2H), 1.53 (s, 9H).

Step B:

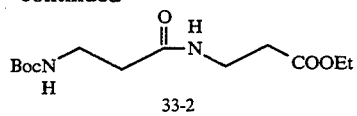

-continued

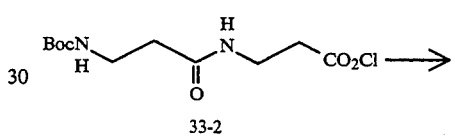

33-2

The Boc amino acid 33-1 (4.50 g, 23.8 mmol), tetrahydrofuran (50 mL), and triethylamine (3.32 mL, 23.8 mmol) were combined and the solution cooled in an ice/acetone bath under argon with stirring. Isobutyl chloroformate (3.12 mL, 23.8 mmol) was added via an addition funnel, the reaction mixture stirred 30 min. Separately β-Alanine ethyl ester hydrochloride (3.86 g, 23.8 mmol), tetrahydrofuran (50 mL), and triethylamine (3.32 mL, 23.8 mmol) were combined and added to the mixed anhydride. The reaction mixture was stirred at room temperature for 18 h, the solid separated by filtration and the filtrate evaporated. The resulting oil was purified by flask column chromatography to afford the product 33-2 (4.27 g, 62%).

$^1$H NMR (CDCl$_3$) δ: 6.20 (s, br, 1H), 5.20 (s, br, 1H), 4.15 (m, 2H), 3.52 (m, 2H), 3.39 (m, 2H), 2.53 (t, J=5.95 Hz, 2H), 2.38 (m, 2H), 1.43 (s, 9H), 1.27 (t, J=6.83 Hz, 3H).

Step C:

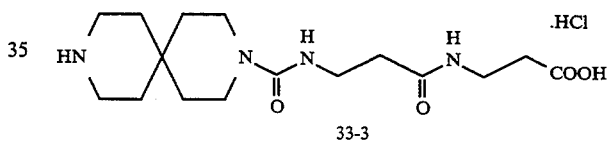

33-2

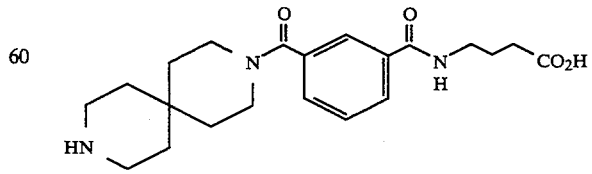

33-3

The Boc group of 33-2 was removed as described previously and the resulting amine converted to urea and deprotected as described in Example 32.

M.P.: 105°–110° C. CHN: Calculated for $C_{16}H_{28}N_4O_4 \cdot HCl \cdot 1.90\ H_2O \cdot 0.40$ EtOAc C, 47.36%; H, 8.13%; N, 12.05%. Found: C, 46.95%; H, 7.53%; N, 12.05%.

$^1$H NMR (DMSO-d6) δ: 8.87 (s, br, 3H), 7.95 (t, J=5.37 Hz, 1H), 3.20 (m, 8H), 2.98 (s, br, 4H), 2.34 (t, J=7.08 Hz, 2H), 2.19 (t, J=7.08 Hz, 2H), 1.62–1.50 (m, 4H), 1.38–1.30 (m, 4H).

EXAMPLE 34

4-[3-(3,9-diazaspiro[5.5]undecane-3-carbonyl)-benzoylamino]butyric acid

This compound was prepared using substantially the procedures described in Example 6.

CHN: Anal Calcd for $C_{21}H_{29}N_3O_4 \cdot 2.05\ H_2O$ C, 59.42; H, 7.88; N, 9.90. Found: C, 59.39; H, 7.43; N, 9.76. MS Pos FAB. 388=M$^+$+1

NMR (300 MHz, D$_2$O): δ(7.69, m, 1H); 7.56 (d, 1H), 7.43 (d, 2H), 3.57 (m 2H), 3.23 (m, 4H), 3.04 (m, 4H), 2.16 (m, 2H), 1.52–1.72 (m, 8H), 1.39 (m, 2H).

What is claimed is:

1. A compound having the formula

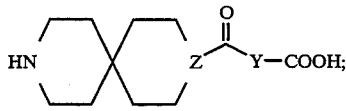

wherein
Z is a nitrogen atom or a carbon atom; and
Y is
C$_{2-4}$ alkylenecarbonylamino C$_{1-3}$ alkylene, substituted or unsubstituted with
phenyl C$_{1-2}$ alkyl,
indolyl C$_{1-2}$ alkyl,
C$_{1-6}$ alkylsulfonamino, or
arylsulfonamino;
C$_{2-4}$ alkylenecarbonylcyclo (amino C$_{2-4}$ alkylene);
C$_{4-7}$ alkylene;
C$_{0-4}$ alkylenephenyl C$_{0-4}$ alkylene;
phenylsulfonylamino C$_{1-3}$ alkylene, substituted or unsubstituted with
C$_{1-3}$ alkyl,
C$_{1-4}$ alkylsulfonylamino, or
C$_{1-2}$ alkylphenylsulfonylamino;
phenylthio C$_{1-3}$ alkylene;
phenylcarboxy C$_{1-3}$ alkylene;
phenyl C$_{2-4}$ alkylene, substituted or unsubstituted with
C$_{2-4}$ alkylsulfonylamino;
phenylcarbonylamino C$_{1-3}$ alkylene, substituted or unsubstituted with
phenyl C$_{1-2}$ alkyl,
C$_{1-4}$ alkylsulfonylamino,
C$_{1-3}$ alkyl;
phenylcarbonylcyclo (amino C$_{2-4}$ alkylene);
phenylhydroxy C$_{2-4}$ alkylene;
amino C$_{1-7}$ alkylene, substituted or unsubstituted with
phenyl C$_{1-2}$ alkyl;
amino C$_{1-2}$ alkylenecarboxyamino C$_{2-3}$ alkyl ene substituted or unsubstituted with
phenyl C$_{1-2}$ alkyl; or
aminophenylcarbonylamino C$_{1-7}$ alkylene
and pharmaceutical salts thereof, and esters thereof.

2. A compound of claim 1 having the formula

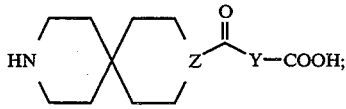

wherein
Z is a nitrogen atom or a carbon atom; and
Y is
i)

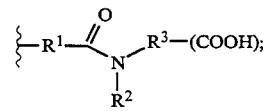

wherein

R$_1$ is C$_{2-4}$alkylene;
R$^2$ is hydrogen or phenylC$_{1-2}$alkylene;
R$_3$ is C$_{1-3}$ alkylene,

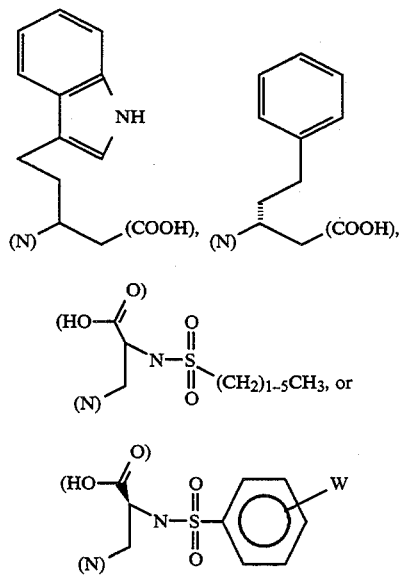

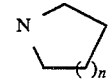

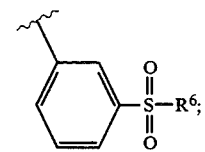

wherein W is H, Me or Cl,
or in combination with R$^2$, forms a heterocyclic ring substituted with COOH, wherein the heterocyclic ring formed by R$^2$ and R$^3$ is

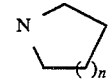

where n is 1–3;
ii) C$_{4-7}$alkylene;
iii) C$_{0-4}$alkylenephenylC$_{0-4}$alkylene;
iv)

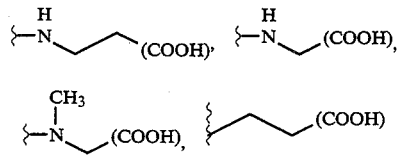

wherein
R$^6$ is

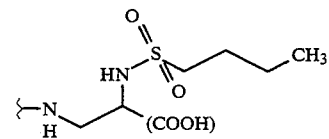

or

-continued

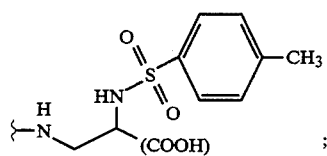

v)

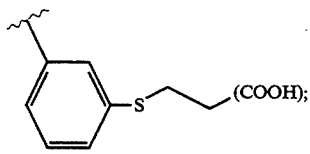

vi)

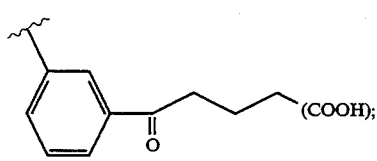

vii)

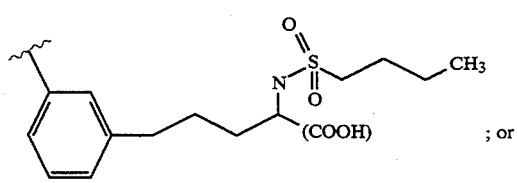

; or viii)

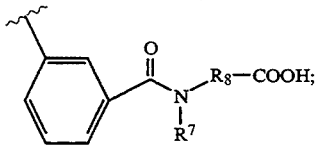

wherein
R⁷ is hydrogen or phenyl C₁₋₂alkyl;
R⁸ is C₁₋₃alkylene;

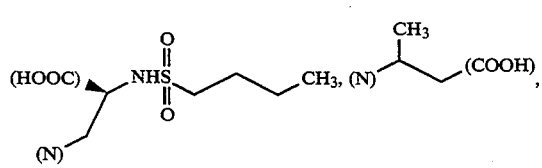

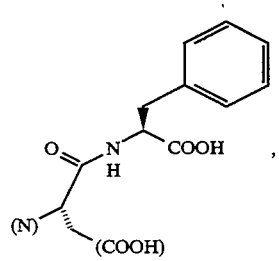

-continued

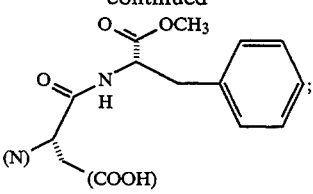

or in combination with R⁷ forms a heterocyclic ring substituted with COOH, wherein the heterocyclic ring formed by R⁷ and R⁸ is

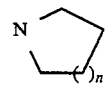

where n is 1–3;

ix)

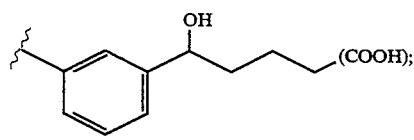

x)

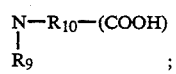

wherein
R⁹ is hydrogen or phenyl C₁₋₂alkylene;
R¹⁰ is

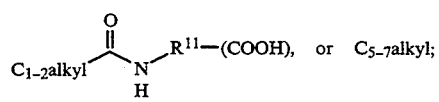

R¹¹ is C₂₋₃alkylene optionally substituted with phenyl C₁₋₂alkyl; and xi)

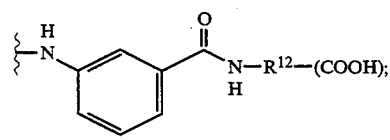

wherein
R¹² is C₁₋₃alkylene
and pharmaceutical salts thereof, and esters thereof.

3. A compound of claim 2 having the formula

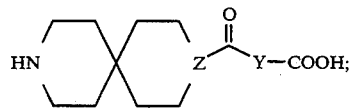

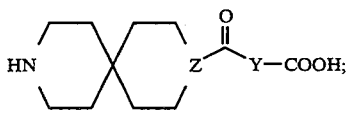

wherein
Z is a nitrogen atom or a carbon atom; and
Y is
i) $C_{0-4}$alkylenephenyl$C_{0-4}$alkylene;
ii)

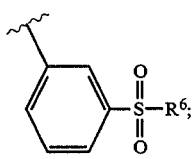

wherein
$R_6$ is

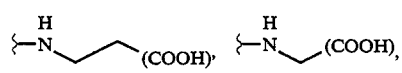

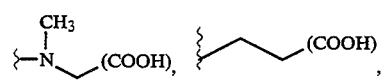

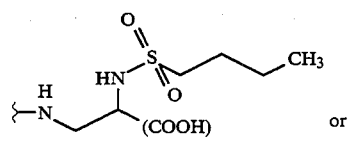

iii)

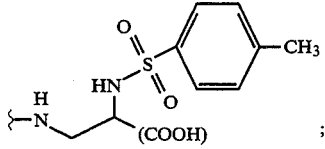

iv)

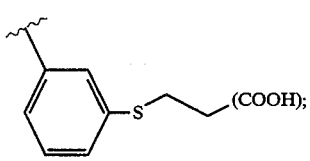

v)

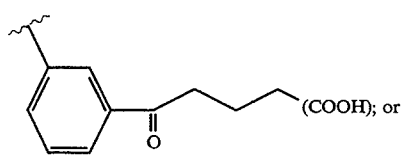

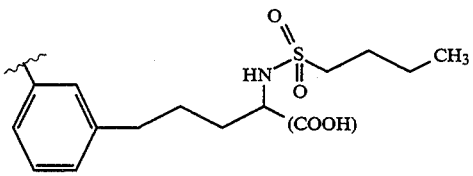

and pharmaceutical salts thereof, and esters thereof.

4. A compound of claim 3 having the formula

wherein
Z is a nitrogen atom; and
Y is $C_{0-4}$alkylenephenyl$C_{0-4}$alkylene;

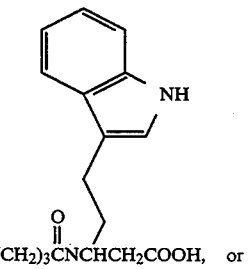

—(CH$_2$)$_3$CNHCHCH$_2$COOH, or

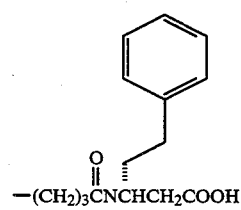

—(CH$_2$)$_3$CNHCHCH$_2$COOH and pharmaceutical salts thereof, and esters thereof.

5. A compound of claim 3 having the formula

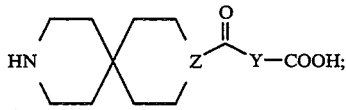

wherein
Z is a carbon atom; and
Y is
i) $C_{1-4}$alkylenephenyl$C_{0-2}$alkylene;
ii)

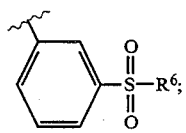

wherein
$R^6$ is

81
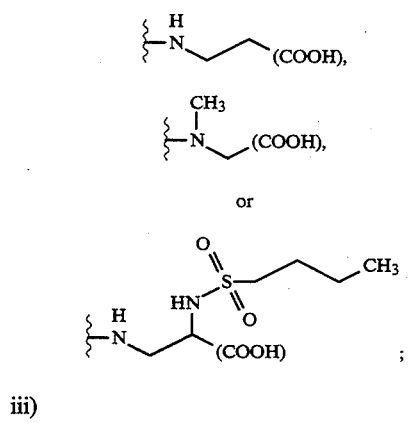
iii)
82
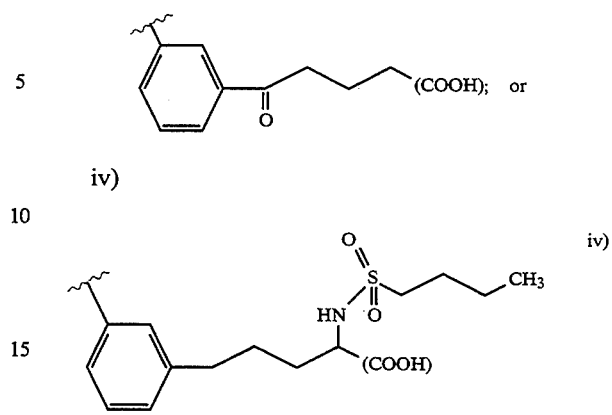
and pharmaceutical salts thereof, and esters thereof.
6. A compound of claim 1 which is selected from
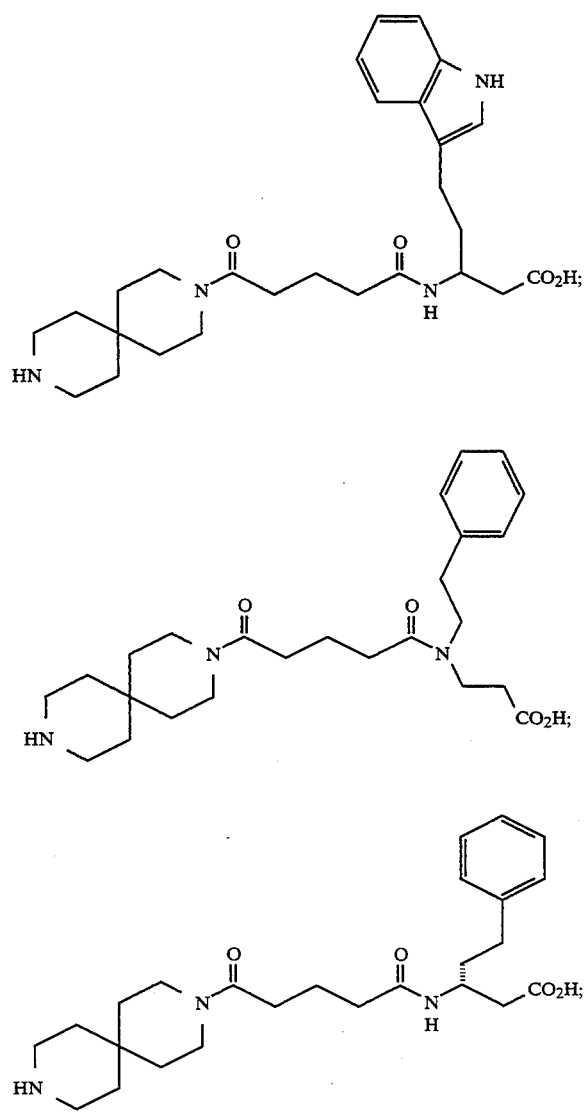

-continued
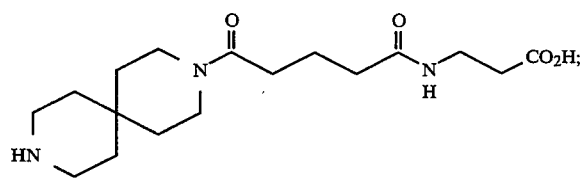
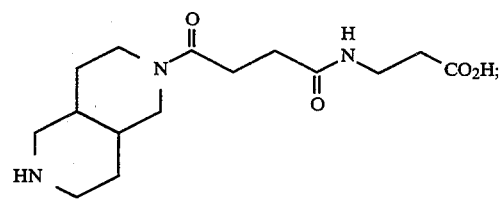
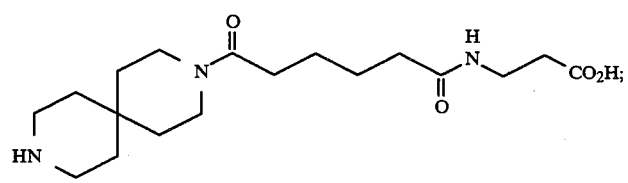
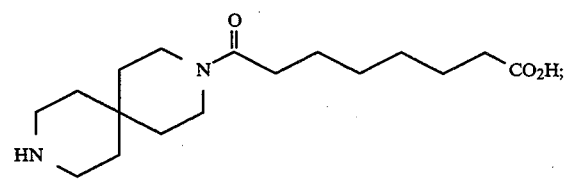
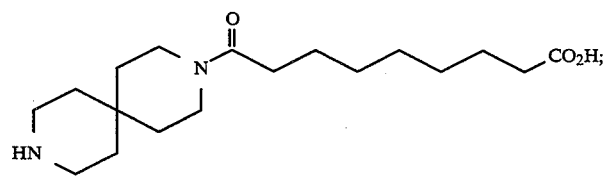
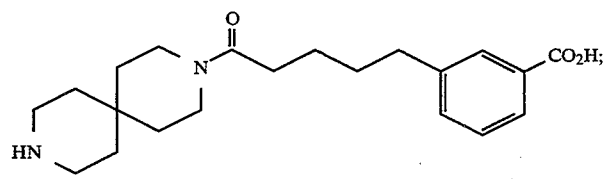
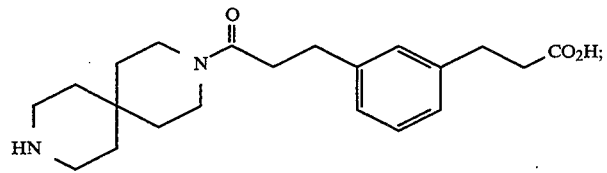
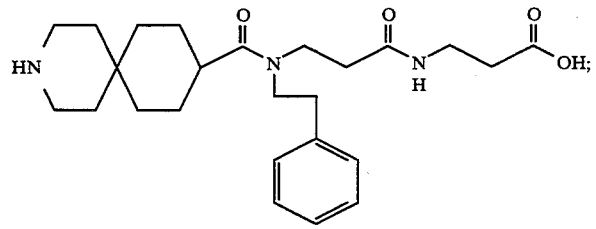

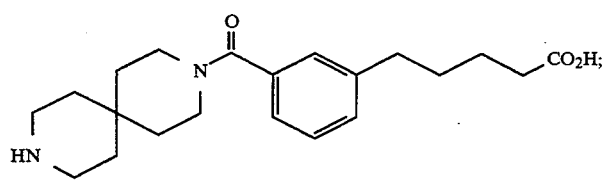
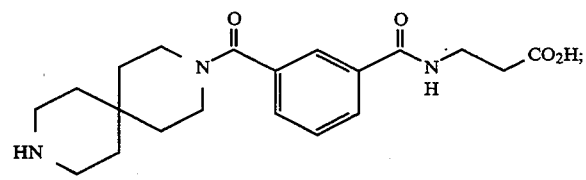
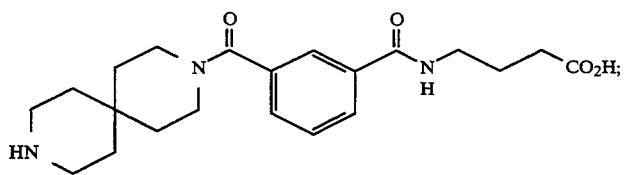
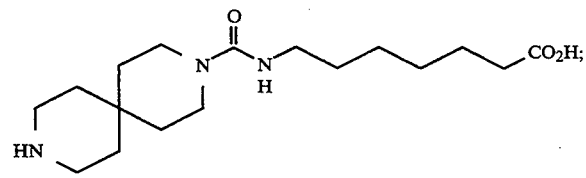
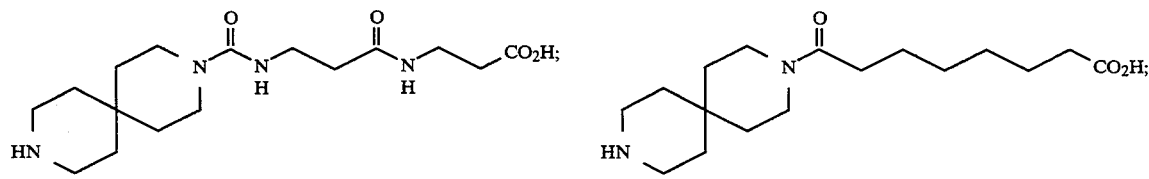
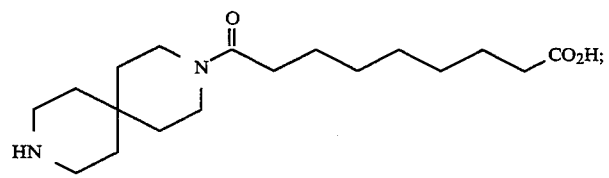
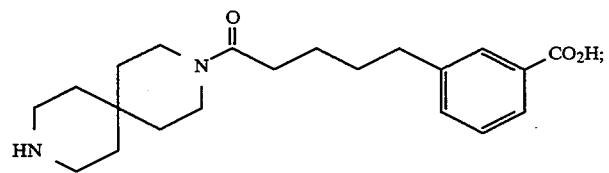
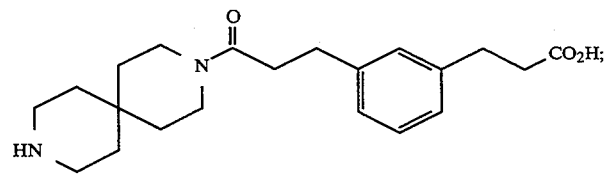

-continued
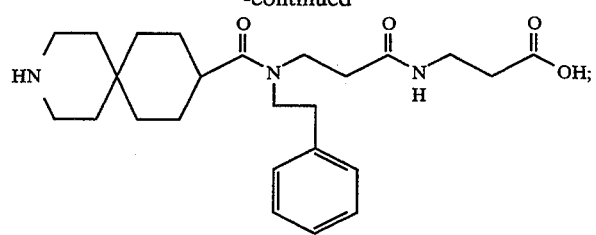
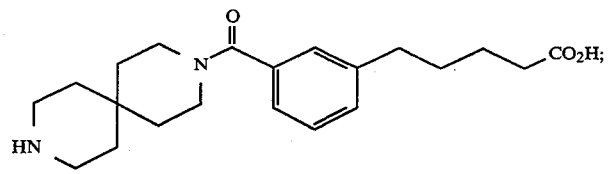
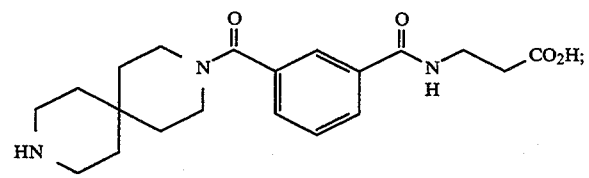
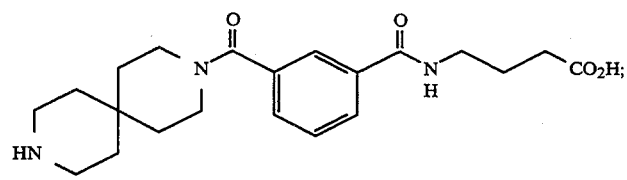
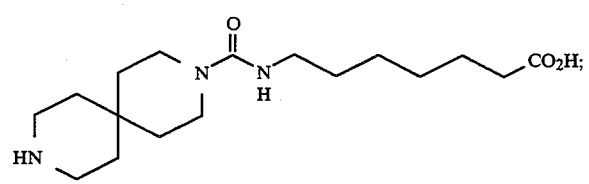
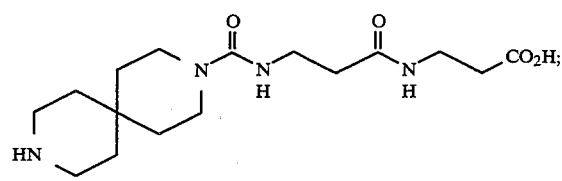
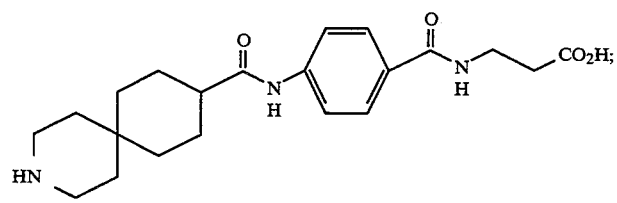
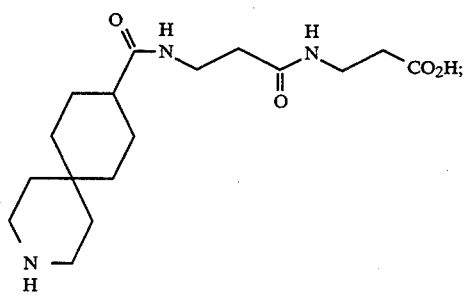
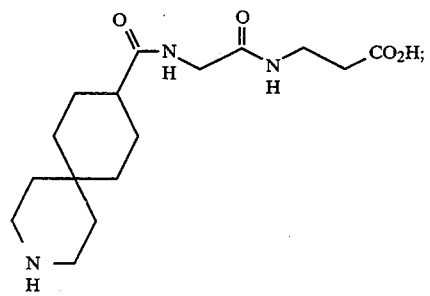

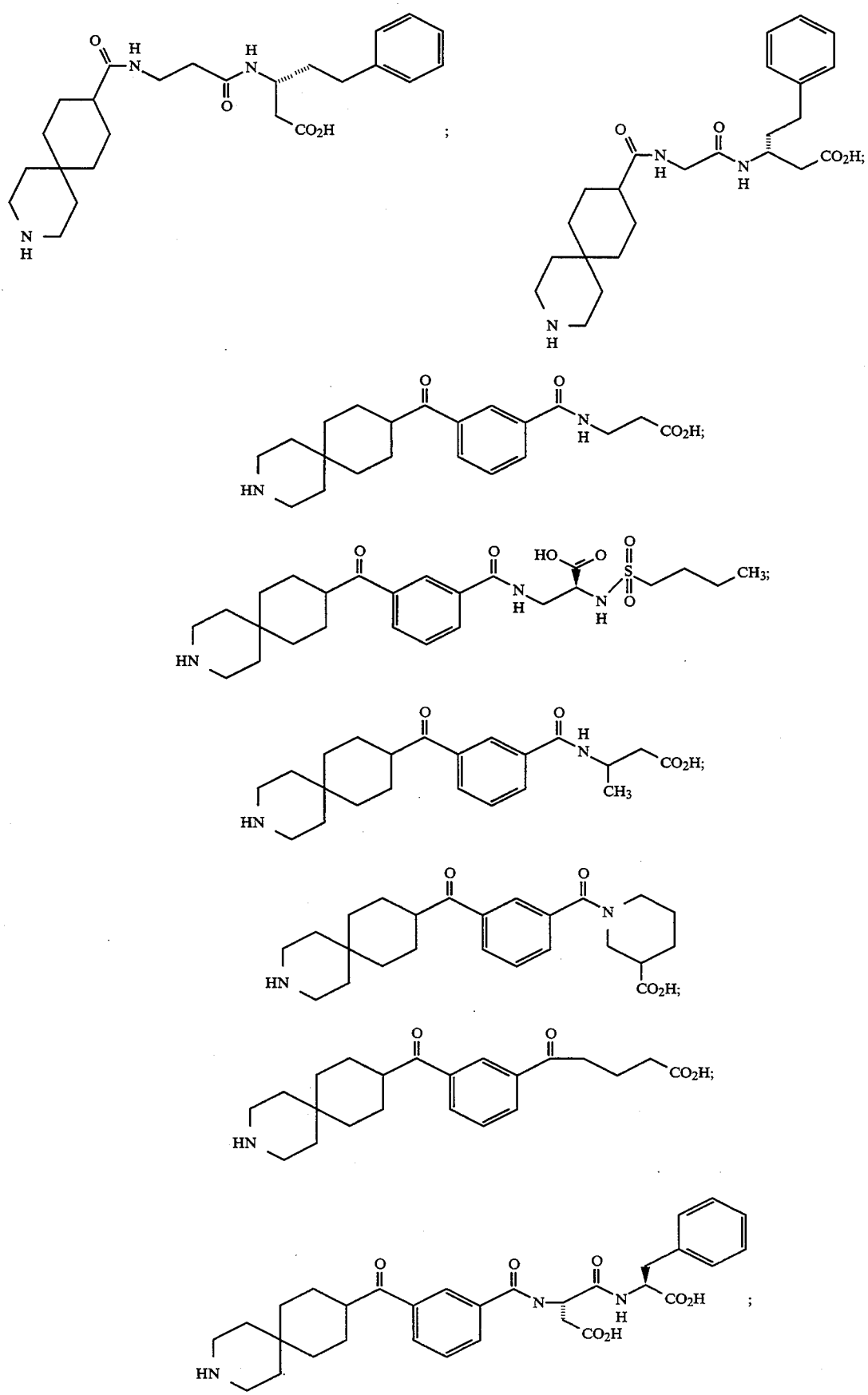

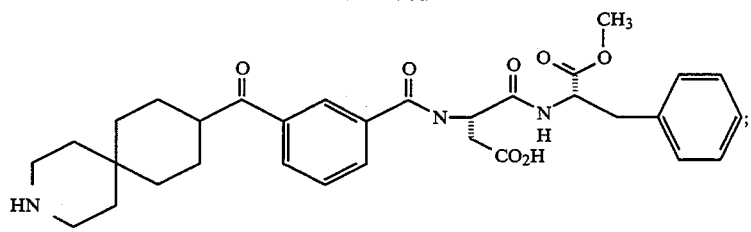
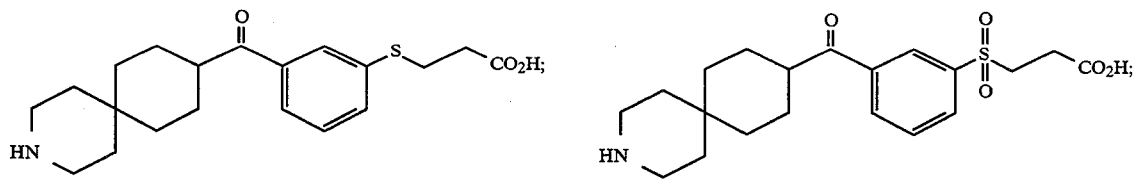
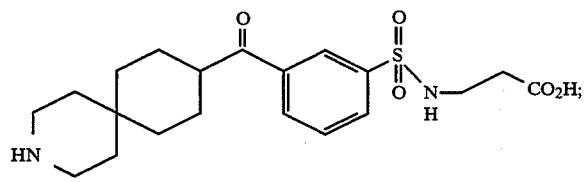
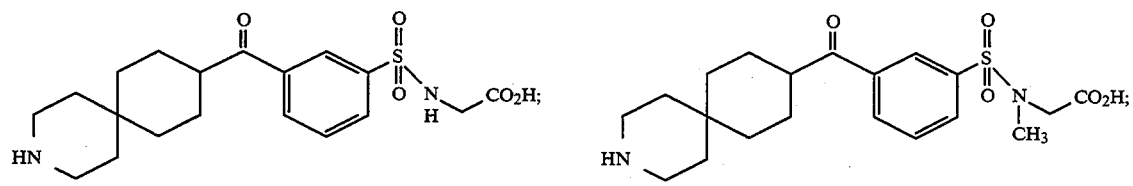
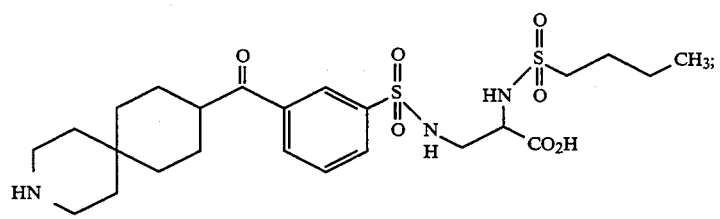
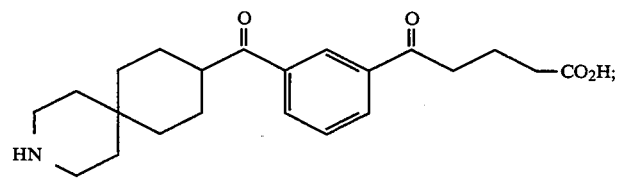
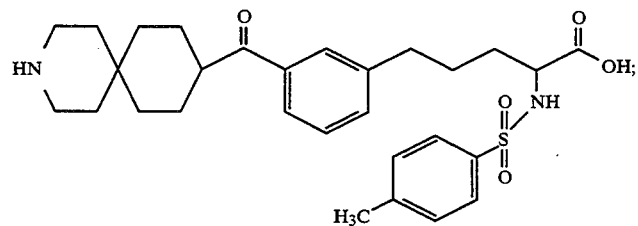
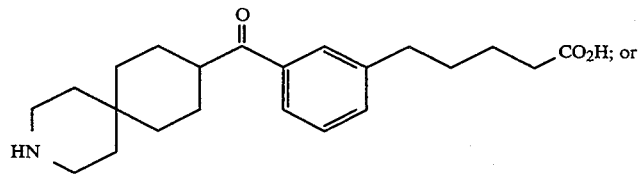

-continued

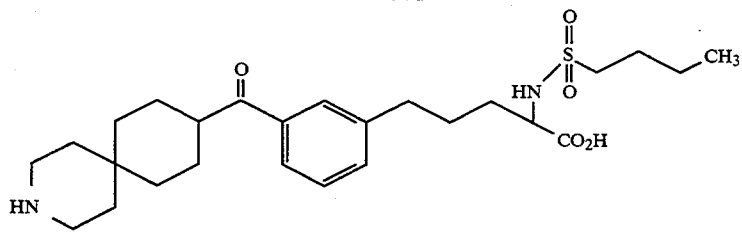

and pharmaceutical salts thereof, and esters thereof.

7. A compound of claim 6 selected from the group consisting of

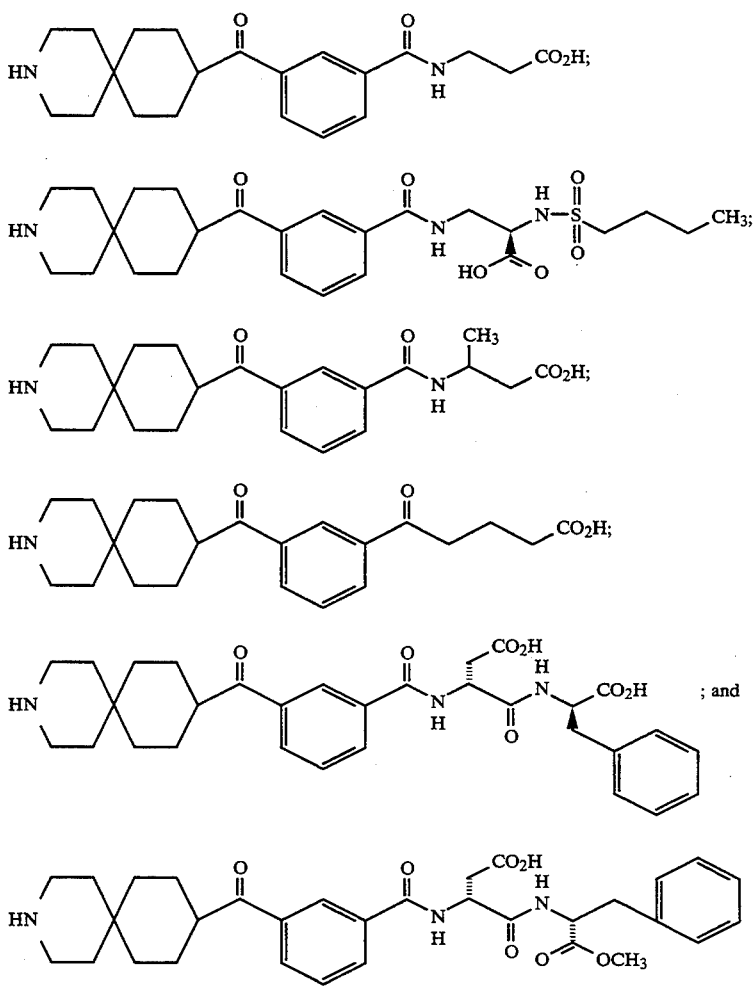

pharmaceutical salts thereof, and esters thereof.

8. A composition for inhibiting the binding of fibrinogen to blood platelets in a mammal, comprising a compound of claim 1 and a pharmaceutically acceptable carrier.

9. A composition for inhibiting the aggregation of blood platelets in a mammal, comprising a compound of claim 1 and a pharmaceutically acceptable carrier.

10. A composition for inhibiting the aggregation of blood platelets in a mammal, comprising a compound of claim 1 in combination with a thrombolytic agent and a pharmaceutically acceptable carrier.

11. A composition for inhibiting the aggregation of blood platelets in a mammal, comprising a compound of claim 1 in combination with an anticoagulant agent and pharmaceutically acceptable carrier.

12. A method for inhibiting the binding of fibrinogen to blood platelets in a mammal, comprising administering to the mammal a composition of claim 8.

13. A method for inhibiting the aggregation of blood platelets in a mammal, comprising administering to the mammal a composition of claim 9.

14. A method for inhibiting the aggregation of blood platelets in a mammal, comprising administering to the mammal a composition of claim 10.

15. A method for inhibiting the aggregation of blood platelets in a mammal, comprising administering to the mammal a composition of claim 11.

16. A composition for inhibiting the binding of fibrinogen to blood platelets, in a mammal, comprising a compound of claim 6 and a pharmaceutically acceptable carrier.

17. A composition for inhibiting the aggregation of blood platelets, in a mammal, comprising a compound of claim 6 and a pharmaceutically acceptable carrier.

18. A method for inhibiting the binding of fibrinogen to blood platelets in a mammal, comprising administering to the mammal a composition of claim 16.

19. A method for inhibiting the aggregation of blood platelets in a mammal, comprising administering to the mammal a composition of claim 17.

* * * * *